US012029381B2

United States Patent
Azoulay et al.

(10) Patent No.: US 12,029,381 B2
(45) Date of Patent: Jul. 9, 2024

(54) DEVICES AND METHODS FOR TREATING SKIN TISSUE USING COLD PLASMA

(71) Applicant: Inbar Medical Ltd., Sofia (BG)

(72) Inventors: Moshe Azoulay, Kibbutz Megido (IL); Eliezer Fuchs, Kibbutz Megido (IL)

(73) Assignee: Inbar Medical Ltd., Sofia (BG)

( * ) Notice: Subject to any disclaimer, the term of this patent is extended or adjusted under 35 U.S.C. 154(b) by 955 days.

(21) Appl. No.: 17/016,837

(22) Filed: Sep. 10, 2020

(65) Prior Publication Data

US 2021/0401480 A1 Dec. 30, 2021

(30) Foreign Application Priority Data

Jun. 25, 2020 (EP) .................................... 20182205

(51) Int. Cl.
*A61B 18/14* (2006.01)
*A45D 29/00* (2006.01)
(Continued)

(52) U.S. Cl.
CPC ............ *A61B 18/042* (2013.01); *A45D 29/00* (2013.01); *A45D 44/00* (2013.01);
(Continued)

(58) Field of Classification Search
CPC ........ A61B 18/042; A61B 2017/00172; A61B 2017/0046; A61B 2018/0047;
(Continued)

(56) References Cited

U.S. PATENT DOCUMENTS 6,518,538 B2 2/2003 Bernabei
8,388,618 B2 * 3/2013 Fridman .............. A61B 18/042
606/49

(Continued)

FOREIGN PATENT DOCUMENTS

WO 2011061476 A1 5/2011
WO 2014181279 A1 11/2014
WO 2019147568 A1 8/2019

OTHER PUBLICATIONS

Http://en.wikipedia.org/wiki/Hyfrecator, donwloaded from internet on Nov. 9, 2020, 4 pp.
(Continued)

*Primary Examiner* — Michael F Peffley
(74) *Attorney, Agent, or Firm* — The Roy Gross Law Firm, LLC; Roy Gross

(57) ABSTRACT

Disclosed herein is a system for treating skin and/or nails with cold plasma. The system includes a discharge device, which includes a handle and an applicator mounted thereon, and control infrastructure, which includes a waveform generator. The applicator includes an elongated tube housing therein a cathode. The handle includes a flyback amplifier. The waveform generator is configured to induce the flyback amplifier to establish a voltage at the cathode. The voltage produced by the flyback amplifier is configured to allow generating a self-sustaining Townsend avalanche when a distal end of the tube is positioned sufficiently near a target site on a skin surface or a nail of a subject, such as to produce a cold plasma discharge directed at the target site and having an average power between about 0.1 μW and about 10 μW, so that the target site is not heated.

19 Claims, 17 Drawing Sheets

(51) Int. Cl.
*A45D 44/00* (2006.01)
*A61B 18/04* (2006.01)
*A61B 17/00* (2006.01)
*A61B 18/00* (2006.01)

(52) U.S. Cl.
CPC ............ *A45D 2200/20* (2013.01); *A61B 2017/00172* (2013.01); *A61B 2017/0046* (2013.01); *A61B 2018/0047* (2013.01); *A61B 2018/0072* (2013.01); *A61B 2018/00767* (2013.01); *A61B 2018/0091* (2013.01)

(58) Field of Classification Search
CPC ........... A61B 2018/00583; A61B 2018/00702; A61B 2018/00732; A61B 2018/00761; A61B 2018/00767; A61B 2018/0091; A61B 2018/00922; A61B 2018/00958; A45D 2200/20; A45D 29/00; A45D 44/00
See application file for complete search history.

(56) References Cited

U.S. PATENT DOCUMENTS

| | | | | |
|---|---|---|---|---|
| 8,575,843 | B2* | 11/2013 | Moore | ............... H05H 1/30 |
| | | | | 315/111.21 |
| 9,005,188 | B2 | 4/2015 | Wandke et al. | |
| 9,060,765 | B2* | 6/2015 | Rencher | ............ A61B 18/1402 |
| 9,384,947 | B2 | 7/2016 | Watson et al. | |
| 9,993,282 | B2 | 6/2018 | Sheperak | |
| 10,213,614 | B2* | 2/2019 | Keidar | ................. A61B 18/042 |
| 10,513,790 | B2* | 12/2019 | Fortin | ................. H05H 1/2406 |
| 2010/0296977 | A1 | 11/2010 | Hancock | |
| 2013/0199540 | A1* | 8/2013 | Buske | ...................... H05H 1/42 |
| | | | | 128/845 |
| 2014/0074090 | A1* | 3/2014 | Lam | .................... A61B 18/042 |
| | | | | 606/49 |
| 2016/0030760 | A1* | 2/2016 | Srb | ...................... H05H 1/2406 |
| | | | | 604/24 |
| 2016/0193475 | A1* | 7/2016 | Srb | ...................... H05H 1/2406 |
| | | | | 604/23 |
| 2016/0338755 | A1 | 11/2016 | Holbeche et al. | |

OTHER PUBLICATIONS

Http://en.wikipedia.org/wiki/Townsend_discharge, downloaded from internet on Nov. 9, 2020, 7 pp.
Thiel, RJ (1998) Bioelectrical Stimulation for People with Patterns Consistent with Certain Chronic Infections, ANMA Monitor 2(4):5-9.
Bernhardt, J (1979) The direct influence of electromagnetic fields on nerve and muscle cells of man within the frequency range of 1Hz to 30MHz, Radiat Environ Biophys 16:309-323.
Jacobson et al (1995) A physical mechanism in the treatment of neurologic disorders with externally applied pico Tesla magnetic fields, Panminerva Med. 37(2):98-104.
Schoenbach et al (2001) Intracellular effect of ultra-short pulses, Bioelectromagnetics, vol. 22:440-448.
Buescher et al (2003) Effects of submicrosecond, high intensity pulsed electric fields on living cells-intra-cellular electromaipulation, Dielectrics and Electrical Insulation, IEEE Transactions, vol. 10:788-794.
Beal, J (1996) Biosystem Liquid Crystals, Several hypotheses relating to interacting mechanisms which may explain biosystem and human hypersensitivities to electric and magnetic fields (http://www.mesaproject.com/index2.php?option-com_content&do_pdf-1&id-91).
Adey, WR (1993) Biological Effects of Electromagnetic Fields, Journal of Cellular Biochemistry 51:410-416.
Wang, Shouguo (2018) A Single Electrode Plasma Discharge Tube Device, EuroSciCon, Prague, Czech Republic, Jul. 16-17, 2018, Am J Compt Sci Inform Technol, vol. 6.
PCT International Search Report for International Application No. PCT/IL2021/050768 dated Oct. 17, 2021.
PCT Written Opinion for International Application No. PCT/IL2021/050768 dated Oct. 17, 2021.

* cited by examiner

DEVICES AND METHODS FOR TREATING SKIN TISSUE USING COLD PLASMA

CROSS REFERENCE TO RELATED APPLICATIONS

This application claims the benefit of priority of European Patent Application No. EP20182205.3, filed on Jun. 25, 2020. The contents of the above applications are all incorporated by reference as if fully set forth herein in their entirety.

TECHNICAL FIELD OF THE INVENTION

The present disclosure relates generally to treatment of skin conditions using cold plasma.

BACKGROUND OF THE INVENTION

Skin growths and abnormalities, such as viral warts, skin tags, pigmentation, and moles—whether for dermatological, medical or aesthetic reasons—are often removed using ablation. Ablation techniques include application of laser radiation, radiofrequency (RF) alternating currents, and liquid nitrogen. Drawbacks of ablation include the formation of a wound at, and often around, the target site, and scarring.

Use of plasma has been suggested for treatment of skin cancer and wounds. U.S. Pat. No. 9,993,282 to Sheperak discloses a plasma generating device that utilizes a cold plasma to contain and direct a stream of electrons with a hand held nozzle to enhance healing of wounds and skin surface abnormalities, and to kill pathogens on skin surfaces in humans and animals wounds, abnormalities and pathogens.

U.S. Pat. No. 10,213,614 to Keidar et al. discloses a device that uses cold plasma to treat cancerous tumors. The device has a gas supply tube with a delivery end. The gas supply tube is configured to carry a gas to the delivery end. A syringe is provided having an opening. The syringe is connected to the supply tube and configured to carry the gas to the opening. A first electrode is positioned inside said syringe, and a second electrode is positioned adjacent to the opening. The first and second electrodes excite the gas to enter a cold plasma state prior to being discharged from the opening of the syringe. An endoscopic tube can be used instead of the syringe. An exhaust tube can be provided to remove gas introduced into the body cavity by the cold plasma jet.

SUMMARY OF THE INVENTION

Aspects of the disclosure, according to some embodiments thereof, relate to devices and methods for treatment of dermatological diseases and disorders, including skin and nail conditions, using cold plasma. More specifically, but not exclusively, aspects of the disclosure, according to some embodiments thereof, relate to devices and methods for treatment of non-malignant skin growths and abnormalities, and nail fungus infections, using cold plasma at skin-temperature. Skin growths and abnormalities treatable using the disclosed devices and methods include, but are not limited to, topical external disorders, such as, skin lesion, skin tags, pigmentation, moles, viral warts, acne, ulcers, and other types of lesions and wounds. Further, the disclosed devices may also be employed for cosmetic (aesthetic) treatments, such as skin rejuvenation and removal or softening of wrinkles.

Advantageously, according to some embodiments, the devices and methods of the present disclosure are non-invasive with the plasma discharge being directed through ambient air, or a reduced pressure environment, onto the treated site. Further, the applied plasma discharge may be at skin temperature (e.g. between 30° and 32°), or lower, so that the subject experiences no pain or discomfort and anesthesia is unnecessary. In contrast to standard plasma-based devices and treatments, the disclosed devices and methods allow for the application of low current (on the order of microamperes) plasma discharges onto the treated site. More specifically, according to some embodiments, the plasma discharge is induced by a self-sustaining Townsend avalanche, thereby allowing for high-degree of control over electrical parameters characterizing the plasma discharge. According to some embodiments, a dielectric barrier may be employed to provide extra control over the plasma discharge. That is to say, a dielectric barrier discharge (DBD) device may be employed, such that the plasma discharge, applied through the ambient air (i.e. the atmospheric pressure air in the region of the treated site) onto the treated site, is induced by a single-electrode plasma-discharge tube filled with an inert gas or a gas mixture including an inert gas at sub-atmospheric pressure.

Crucially, in contrast to many widely-employed treatment methods, such as laser-based methods and intense pulsed light (IPL) methods, the devices and methods of the present disclosure are effective not only for light skin tones but also for dark skin tones.

As a further advantage, according to some embodiments, a single treatment may suffice to remove a skin growth/abnormality, with the treatment being of short duration, typically lasting a few minutes, e.g. less than ten minutes or even less than five minutes. Moreover, as exemplified herein, the disclosed devices and methods induce healing of the skin, and do not induce necrosis, infections or burns, thereby rendering redundant the use of disinfectants and support creams/ointments, such as burn treatment creams/ointments. Consequently, the treated site may be left substantially unscarred.

Thus, according to an aspect of some embodiments, there is provided a system for treating skin and/or nails with cold plasma. The system includes a discharge device and control infrastructure. The discharge device includes a handle and an applicator. The and control infrastructure includes a waveform generator. The applicator includes an elongated tube. The tube extends from a tube proximal end to a tube distal end. The tube includes a cathode housed within the tube. The tube is mounted, via the tube proximal end, on a distal tip portion of the handle. The handle includes a flyback amplifier functionally associated with the waveform generator and electrically associated with the cathode (and an anode). The waveform generator is configured to induce the flyback amplifier to apply a voltage at the cathode (i.e. establish a voltage between the cathode and the anode). The voltage produced by the flyback amplifier is configured to allow generating a self-sustaining Townsend avalanche when the tube distal end is positioned sufficiently near a target site on a skin surface or a nail of a subject, such as to produce a cold plasma discharge directed at the target site. The produced cold plasma discharge has an average electrical current amplitude in the range of about 0.1 mA to about 10 mA and/or an average power in the range of about 0.1 μW to about 10 μW. The system is thereby configured to treat the target site without heating thereof.

According to some embodiments, the waveform generator and the flyback amplifier are electrically coupled. The flyback amplifier is configured to amplify a voltage signal produced by the waveform generator, such that an instantaneous magnitude of the voltage applied at the cathode is dependent on the instantaneous magnitude of the voltage signal.

According to some embodiments, the flyback amplifier is a step-up transformer.

According to some embodiments, the voltage applied at the cathode is characterized by a series of (voltage) pulses having a duty cycle in the range of 1% to 70%. Each pulse may have a pulse width in the range of about 10 nsec to about 200 nsec, and a frequency spectrum including one or more frequencies in the range of about 10 kHz to about 1 GHz.

According to some embodiments, one or more of the pulses in the series of pulses are amplitude modulated, double-modulated, or harmonically modulated, and/or one or more of the pulses in the series of pulses are amplitude modulated by a monotonically decreasing function.

According to some embodiments, the tube is closed on the tube distal end and includes an inert gas and/or air at a sub-atmospheric pressure of at least about 2 kPa or higher.

According to some embodiments, dimensions and shape of the tube distal end are adapted to a group of lesions or a group of nails having common dimensions, shape, and/or texture.

According to some embodiments, the cathode includes a transversely extending surface, which extends over at least about 25% of a transverse cross-section of the tube. The applicator is thereby configured for dielectric-barrier discharge.

According to some embodiments, the cathode includes a needle (also referred to as "needle member") extending longitudinally within the tube, and/or the applicator further includes an electrically-conducting collimator, which is mounted on the tube distal end. The discharge device is thereby configured for corona discharge or spark discharge.

According to some embodiments, the control infrastructure further includes a vacuum pump fluidly coupled to the tube via an applicator gas port on the tube proximal end, such as to allow withdrawing gas from the tube.

According to some embodiments, the tube distal end is open and configured to be pressed against skin of a subject around a target site, such as to fluidly seal the tube distal end. The control infrastructure further includes a vacuum pump fluidly coupled to the tube via an applicator gas port on the tube proximal end, such as to allow withdrawing gas from the tube. Optionally, the cathode includes a needle extending longitudinally within the tube.

According to some embodiments, the control infrastructure further includes a gas supply fluidly coupled to the tube via the applicator gas port, such as to allow injecting gas into the tube.

According to some embodiments, the needle is hollow and fluidly coupled to the gas port, such as to allow withdrawal and injection of gas therethrough.

According to some embodiments, the system further includes processing and control circuitry. The handle further includes a user interface configured to allow a user to operate the discharge device. The processing and control circuitry is functionally associated with the waveform generator, the flyback amplifier, and the user interface. The processing and control circuitry is configured to coordinate operations of the waveform generator, the flyback amplifier, and the user interface. The processing and control circuitry is further configured to allow the user, via the user interface, to set and/or adjust electrical parameters characterizing the cold plasma discharge.

According to some embodiments, the electrical parameters include one or more of an average power of the cold plasma discharge, an average electrical current amplitude, a frequency or frequencies of the pulses, a waveform or waveforms of the pulses, a duration or durations of the pulses, and a separation or separations between pairs of adjacent pulses.

According to some embodiments, the handle further includes a camera positioned to be at a line-of-sight from the target site when the handle is properly positioned with respect to the target site, such as to allow generating a cold plasma discharge directed at the target site. The camera is functionally associated with the processing and control circuitry.

According to some embodiments, the system further includes an external controller which includes at least some components of the control infrastructure. The processing and control circuitry include a main control unit, housed in the external controller, and an auxiliary control unit, communicatively associated with the main control unit and housed in the handle. The external controller and the discharge device are functionally associated via a utility cable.

According to some embodiments, the control infrastructure is housed within the handle.

According to some embodiments, the flyback amplifier includes a piezoelectric crystal electrically coupled on a first end thereof to the cathode and on a second end thereof to the anode. The waveform generator is configured to cause the piezoelectric crystal to produce a voltage between the cathode and the anode by generating mechanical signal inducing stress vibrations in the piezoelectric crystal.

According to some embodiments, the system is configured for treating and/or removing one or more of skin lesions, skin tags, pigmentation, moles, viral warts, acne, ulcers, and nails fungus.

According to some embodiments, the system is configured for skin rejuvenation treatments and/or removal or softening of wrinkles treatments.

According to some embodiments, the applicator is detachably mounted on the handle.

According to an aspect of some embodiments, there is provided a kit for treating skin tissue using cold plasma. The kit includes a system for treating skin tissue with cold plasma, as described above, with a detachable applicator, and a set of applicators. Each of the applicators may be configured to treat a respective group of skin or nail diseases and/or disorders having common dimensions, shape, and/or texture.

According to an aspect of some embodiments, there is provided a method of treating skin and/or nail diseases and/or disorders in a target site on a subject. The method includes stages of:

An initial stage including providing a system as described above or a kit as described above.

A preparation stage including positioning the system such that the tube distal end of the applicator is at least in proximity to a target site on a subject.

A treatment stage including closing an electrical circuit through the target site by generating a cold plasma discharge, The cold plasma discharge has an average electrical current amplitude in the range of about 0.1 mA to about 10 mA and/or an average power in the range of about 0.1 µW to about 10 µW, so that the target site is not heated.

According to some embodiments, the cold plasma discharge includes a series of discharge pulses.

According to some embodiments, the series of discharge pulses is induced by applying a voltage at the cap cathode of the applicator characterized by a series of (voltage) pulses having a duty cycle in the range of 1% to 70%. Each pulse may have a pulse width in the range of about 10 nsec to about 200 nsec. A frequency spectrum of each pulse may include one or more frequencies in the range of about 10 kHz to about 1 GHz.

According to some embodiments, one or more of the pulses in the series of pulses are amplitude modulated, double-modulated, or harmonically modulated, and/or wherein one or more of the pulses in the series of pulses are amplitude modulated by a monotonically decreasing function.

According to some embodiments, a duration of the treatment stage is less than about 10 minutes.

According to some embodiments, in the preparation stage, the tube distal end is positioned at no more than 5 mm from the target site.

According to some embodiments, in the treatment stage, the cold plasma discharge is generated by gradually increasing a voltage at the cap cathode of the applicator from an initial value below about 10 kV until the average power is reached.

According to some embodiments, in the treatment stage, the cold plasma discharge is generated by gradually decreasing a distance between the tube distal end and the target site, until the average power is reached.

According to some embodiments, wherein the tube distal end is open, in the preparation stage, the tube distal end is brought into contact with skin surrounding the target site.

According to some embodiments, the preparation stage further includes decreasing a pressure within the applicator to sub-atmospheric pressure.

According to some embodiments, the sub-atmospheric pressure is greater than about 2 kPa.

According to some embodiments, the method further includes an optional stage of repeating the preparation stage and treatment stage at least one additional time.

According to some embodiments, each repetition is performed between 5 to 10 days after a last treatment of the target site.

According to some embodiments, the method further includes a diagnosis stage, performed prior to the preparation and treatment stages, wherein treatment parameters are determined. The treatment parameters at least include one or more plasma parameters of the cold plasma discharge.

According to some embodiments, the treatment stage further includes a monitoring substage and, optionally, a treatment adjustment substage. In the monitoring substage, one or more plasma parameters are monitored. In the treatment adjustment substage, one or more of the treatment parameters are adjusted contingent on at least of the one or more plasma parameters being outside a respective range.

According to some embodiments, the method is configured for treating and/or removing one or more of skin lesions, skin tags, pigmentation, moles, viral warts, acne, ulcers, and nail fungus.

According to some embodiments, the method is further configured for skin rejuvenation treatments and/or removal or softening of wrinkles treatments.

According to some embodiments, there is provided use of the system or the kit disclosed herein, for treatment of skin and nail diseases and disorders in a target site.

According to some embodiments, there is provided a system or a kit, as disclosed herein, for treatment of skin and nail diseases and disorders in a target site, the treatment comprising:
  positioning the system such that the tube distal end of the applicator is at least in proximity to a target site; and
  closing an electrical circuit through the target site by generating a cold plasma discharge;
  wherein the cold plasma discharge has an average electrical current amplitude in the range of about 0.1 mA to about 10 mA and an average power in the range of about 0.1 µW to about 10 µW, and wherein the cold plasma discharge comprises a series of discharge pulses, so that the target site is not heated.

According to some embodiments, the series of discharge pulses is induced by applying a voltage at the cap cathode of the applicator characterized by a series of pulses having a duty cycle in the range of 1% to 70%, wherein each pulse has a pulse width in the range of about 10 nsec to about 200 nsec, and wherein a frequency spectrum of the pulse includes one or more frequencies in the range of about 10 kHz to about 1 GHz; and preferably, wherein one or more of the pulses in the series of pulses are amplitude modulated, double-modulated, or harmonically modulated, and/or wherein one or more of the pulses in the series of pulses are amplitude modulated by a monotonically decreasing function.

According to some embodiments, the treatment further comprises:
  prior to the closing of the electrical circuit, determining treatment parameters, the treatment parameters at least comprising one or more parameters of the cold plasma discharge; and
  subsequently to the closing of the electrical circuit, monitoring one or more plasma parameters, and adjusting one or more of the treatment parameters, contingent on at least one of the one or more monitored plasma parameters being outside a respective range.

Certain embodiments of the present disclosure may include some, all, or none of the above advantages. One or more other technical advantages may be readily apparent to those skilled in the art from the figures, descriptions, and claims included herein. Moreover, while specific advantages have been enumerated above, various embodiments may include all, some, or none of the enumerated advantages.

Unless otherwise defined, all technical and scientific terms used herein have the same meaning as commonly understood by one of ordinary skill in the art to which this disclosure pertains. In case of conflict, the patent specification, including definitions, governs. As used herein, the indefinite articles "a" and "an" mean "at least one" or "one or more" unless the context clearly dictates otherwise.

Unless specifically stated otherwise, as apparent from the disclosure, it is appreciated that, according to some embodiments, terms such as "processing", "computing", "calculating", "determining", "estimating", "assessing", "gauging" or the like, may refer to the action and/or processes of a computer or computing system, or similar electronic computing device, that manipulate and/or transform data, represented as physical (e.g. electronic) quantities within the computing system's registers and/or memories, into other data similarly represented as physical quantities within the computing system's memories, registers or other such information storage, transmission or display devices.

Embodiments of the present disclosure may include apparatuses for performing the operations herein. The apparatuses may be specially constructed for the desired purposes or may include a general-purpose computer(s) selectively activated or reconfigured by a computer program stored in the computer. Such a computer program may be stored in a computer readable storage medium, such as, but not limited to, any type of disk including floppy disks, optical disks, CD-ROMs, magnetic-optical disks, read-only memories (ROMs), random access memories (RAMs), electrically programmable read-only memories (EPROMs), electrically erasable and programmable read only memories (EEPROMs), magnetic or optical cards, or any other type of media suitable for storing electronic instructions, and capable of being coupled to a computer system bus.

The processes and displays presented herein are not inherently related to any particular computer or other apparatus. Various general-purpose systems may be used with programs in accordance with the teachings herein, or it may prove convenient to construct a more specialized apparatus to perform the desired method(s). The desired structure(s) for a variety of these systems appear from the description below. In addition, embodiments of the present disclosure are not described with reference to any particular programming language. It will be appreciated that a variety of programming languages may be used to implement the teachings of the present disclosure as described herein.

Aspects of the disclosure may be described in the general context of computer-executable instructions, such as program modules, being executed by a computer. Generally, program modules include routines, programs, objects, components, data structures, and so forth, which perform particular tasks or implement particular abstract data types. Disclosed embodiments may also be practiced in distributed computing environments where tasks are performed by remote processing devices that are linked through a communications network. In a distributed computing environment, program modules may be located in both local and remote computer storage media including memory storage devices.

BRIEF DESCRIPTION OF THE FIGURES

Some embodiments of the disclosure are described herein with reference to the accompanying figures. The description, together with the figures, makes apparent to a person having ordinary skill in the art how some embodiments may be practiced. The figures are for the purpose of illustrative description and no attempt is made to show structural details of an embodiment in more detail than is necessary for a fundamental understanding of the disclosure. For the sake of clarity, some objects depicted in the figures are not drawn to scale. Moreover, two different objects in the same figure may be drawn to different scales. In particular, the scale of some objects may be greatly exaggerated as compared to other objects in the same figure.

In the figures.

DETAILED DESCRIPTION OF THE INVENTION

Figure 1A:
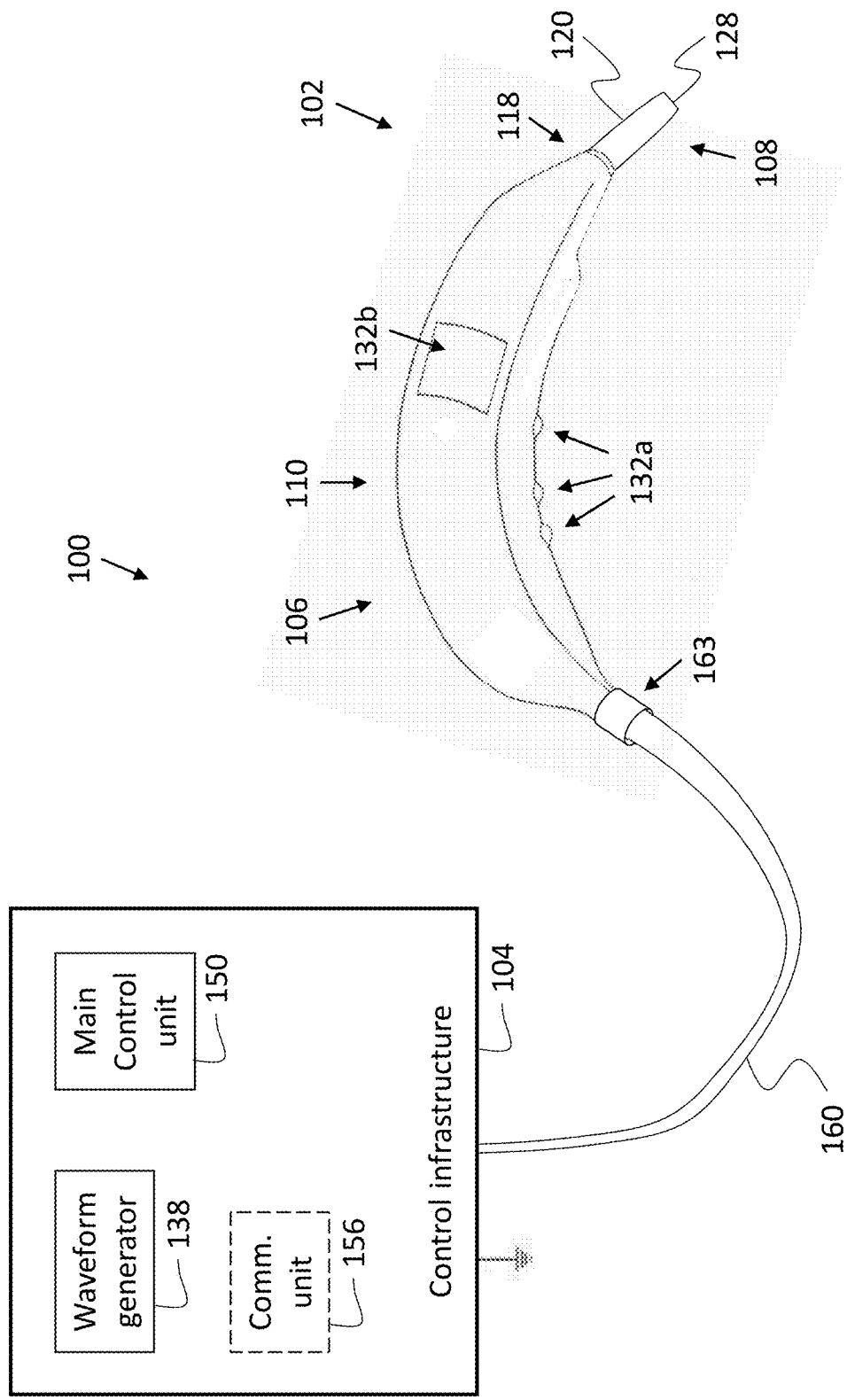
FIG. 1A schematically depicts a system for treating skin tissue and nails using cold plasma, the system includes a cold-plasma discharge device and external control infrastructure, the discharge device includes a handle and a cold-plasma applicator, according to some embodiments.

The principles, uses, and implementations of the teachings herein may be better understood with reference to the accompanying description and figures. Upon perusal of the description and figures present herein, one skilled in the art will be able to implement the teachings herein without undue effort or experimentation. In the figures, same reference numerals refer to same parts throughout.

In the description and claims of the application, the words "include" and "have", and forms thereof, are not limited to members in a list with which the words may be associated.

As used herein, the term "about" may be used to specify a value of a quantity or parameter (e.g. the length of an element) to within a continuous range of values in the neighborhood of (and including) a given (stated) value. According to some embodiments, "about" may specify the value of a parameter to be between 80% and 120% of the given value. For example, the statement "the length of the element is equal to about 1 m" is equivalent to the statement "the length of the element is between 0.8 m and 1.2 m". According to some embodiments, "about" may specify the value of a parameter to be between 90% and 110% of the given value. According to some embodiments, "about" may specify the value of a parameter to be between 95% and 105% of the given value.

As used herein, according to some embodiments, the terms "substantially" and "about" may be interchangeable.

In block diagrams, optional elements and components are delineated by dashed boxes. Similarly, in flow charts, optional stages and substages are delineated by dashed boxes.

As used herein, according to some embodiments, the term "cold plasma" refers to a nonthermal plasma. According to some such embodiments, the term "cold plasma" refers to a nonthermal plasma, which when applied onto a target site on the skin of a patient, such as to close an electric conduction path through the target site, does not, or substantially not, heat target site and the skin tissue surrounding the target site. That is, the temperature of the target site and skin tissue therearound remains unchanged (i.e. at about skin temperature 30°) or substantially unchanged.

As used herein, the terms "treatment site", "treated site", and "target site"—with reference to an area on the skin treated using the disclosed devices and methods—are interchangeable. Similarly, the terms "treated tissue" and "target tissue"—with reference to a tissue at a target site—may be used interchangeably with "treated site" and "target site".

As used herein, the term "gas" also covers air.

Systems

Figure 1B:
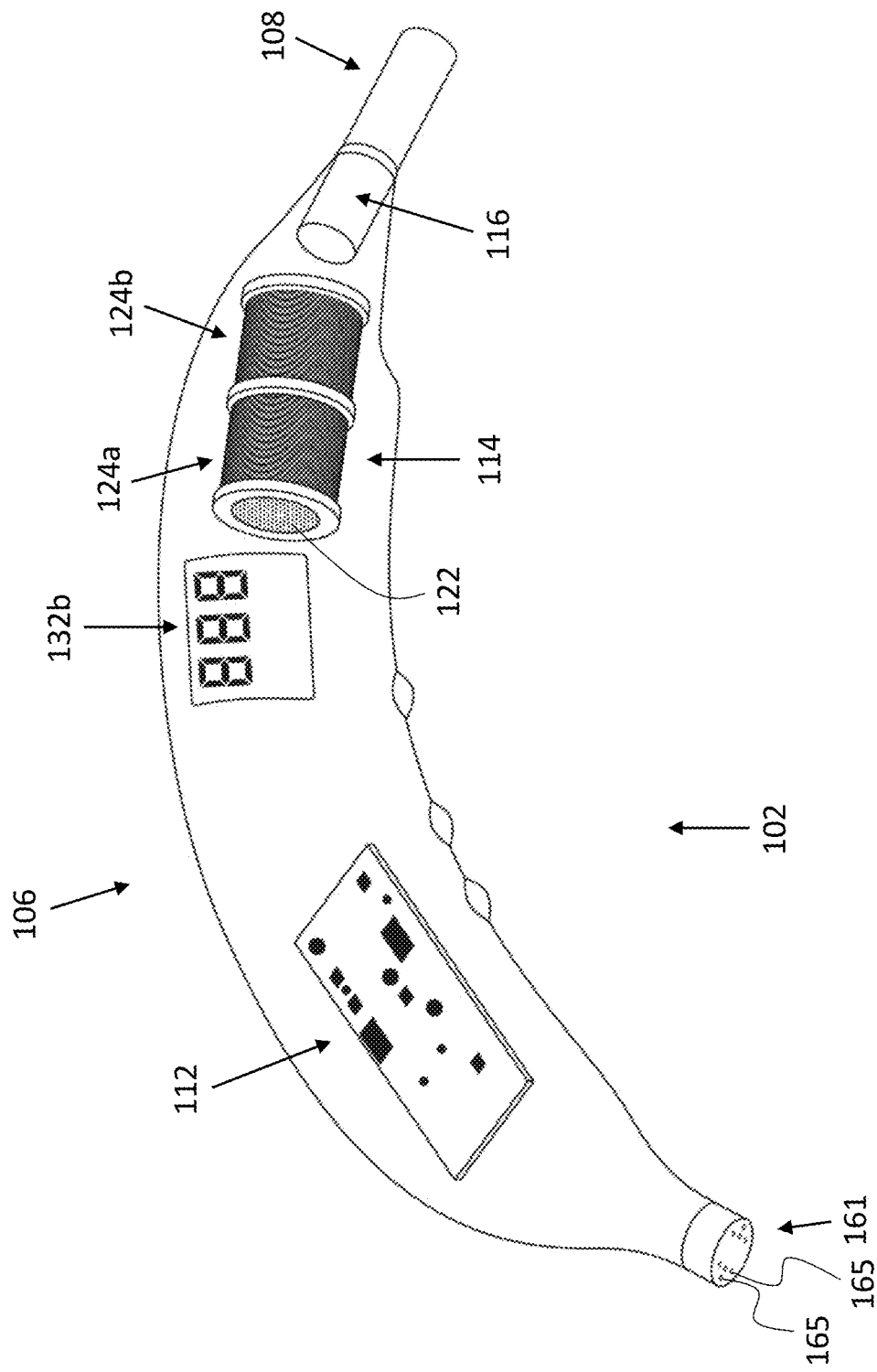
FIG. 1B schematically depicts the discharge device of FIG. 1A, according to some embodiments.

FIG. 1A schematically depicts a cold-plasma discharge system 100 for treatment of non-malignant skin growths and abnormalities, and nail diseases, according to some embodiments. System 100 includes a cold-plasma discharge device 102 and external control infrastructure 104. Discharge device 102 includes a handle 106 and a cold-plasma applicator 108. In FIG. 1B, an outline of a housing 110 of handle 106 is indicated but otherwise housing 110 is depicted as transparent so as to render visible components included therein.

Figure 5A:
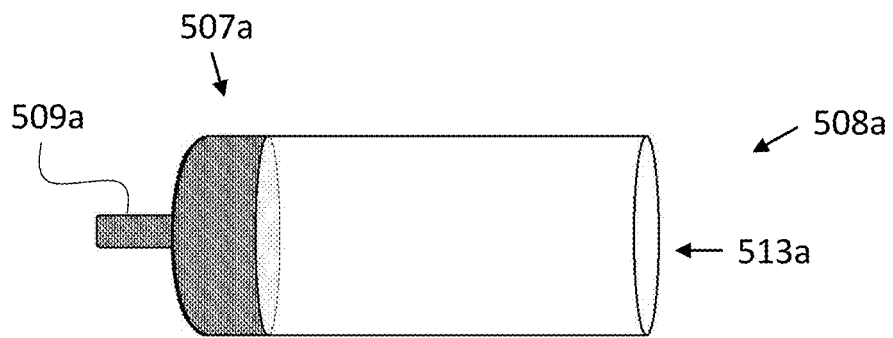
FIGS. 5A-5E schematically depict five different applicators of a cold-plasma discharge device for treating skin tissue and/or nails using cold plasma, according to some embodiments.

Housing 110 includes an (auxiliary) control unit 112, a flyback amplifier 114, and a connector 116. According to some embodiments, housing 110 may be made of an insulating material, such as a polymer (e.g. plastic). Applicator 108 is effectively a single-electrode plasma-discharge tube configured for therapeutic and/or cosmetic applications. More specifically, applicator 108 includes an (applicator) cathode (not shown) mounted on a proximal portion of an electrically insulating and fluidly-sealed tube 120, essentially as depicted in FIG. 5A. Tube 120 may include an inert gas (such as neon or argon) and/or air at sub-atmospheric pressures of at least about 2 kPa or higher (but less than one atmosphere).

Connector 116 may be positioned on a distal tip portion 118 of handle 106. Applicator 108 is mounted on, or configured to be detachably mounted on, connector 116, such as to be electrically connected to connector 116. Connector 116 is electrically coupled to flyback amplifier 114. Flyback amplifier 114 is configured to amplify the amplitude of a voltage signal input thereinto, such as to produce a floating voltage signal at the cathode (more precisely, between the cathode and an associated anode) having an amplitude which may be greater than about 10 kV. The (floating) voltage signal leads to the generation of an electric field at and near the cathode. According to some embodiments, flyback amplifier 114 may be configured to amplify the input voltage signal (i.e. the voltage signal input into flyback amplifier 114), by a factor in the range of about 50 to about 1000. According to some such embodiments, flyback amplifier 114 may be configured to amplify the voltage signal by a factor which is greater than about 300 (for example, about 400). According to some embodiments, flyback amplifier 114 may be a step-up transformer including a ferromagnetic core 122 and a pair of coils: a proximal coil 124a and a distal coil 124b. Each of the coils is winded about core 122. Distal coil 124b includes a greater number of turns (i.e. windings about core 122) than proximal coil 124a, thereby ensuring that the output voltage of distal coil 124b (i.e. the electromotive force induced by the time-varying current flowing through proximal coil 124a) is amplified relative to the input voltage of proximal coil 124a. According to some embodiments, the number of turns in distal coil 124b is greater by a factor of between about 50 and about 1000 than the number of turns in proximal coil 124a, so that the input voltage is amplified by substantially the same factor.

A first end of distal coil 124b is electrically-coupled to the cathode (in applicator 108). A second end of distal coil 124b may be coupled to a ground anode (e.g. a ground terminal of external control infrastructure 104) or may be left exposed (in which case the second end effectively functions as the anode). For convenience, throughout the text the convention is adopted whereby the voltage at the anode is zero. Discharge device 102 is thus configured to indirectly ionize ambient air about a treatment site on the skin such as to produce a cold-plasma discharge directed at the treatment site. More specifically, by applying a sufficiently high voltage at the cathode (i.e. by inducing a sufficiently high voltage between the two ends of distal coil 124b), e.g. above about 10 kV, cold plasma (in the gas) may be generated within tube 120, which in turn may induce generation of cold plasma outside applicator 108, when applicator 108 is close to an electrically conducting medium, or even a weakly conducting medium, such as skin, as explained below. In particular, the voltage selected to achieve a desired average power depends on the electrical impedance at the treated target site. Thus, treatment generally initiates by applying a low voltage (at the cathode), i.e. below 10 kV, the applied voltage is then gradually and gently (slowly) increased, until reaching a desired power.

According to some embodiments, applicator 108 is detachable from handle 106 (that is, from connector 116), thereby allowing (i) to replace applicator 108, for example, in the event of malfunction thereof, and, in particular, (ii) to switch between different applicators. Different applicators may be configured for treating different types of skin conditions (or treating nails), respectively, as elaborated on below. According to some embodiments, and as described in the description of FIGS. 5A-5E, applicator 108 may include a male element and connector 116 may include a female element corresponding to the male element, thereby allowing to mechanically secure (and electrically connect) applicator 108 to connector 116. Alternatively, according to some embodiments, a proximal portion of applicator 108 may include a female element and connector 116 may be in the form of a male element corresponding to the female element.

Figure 5B:
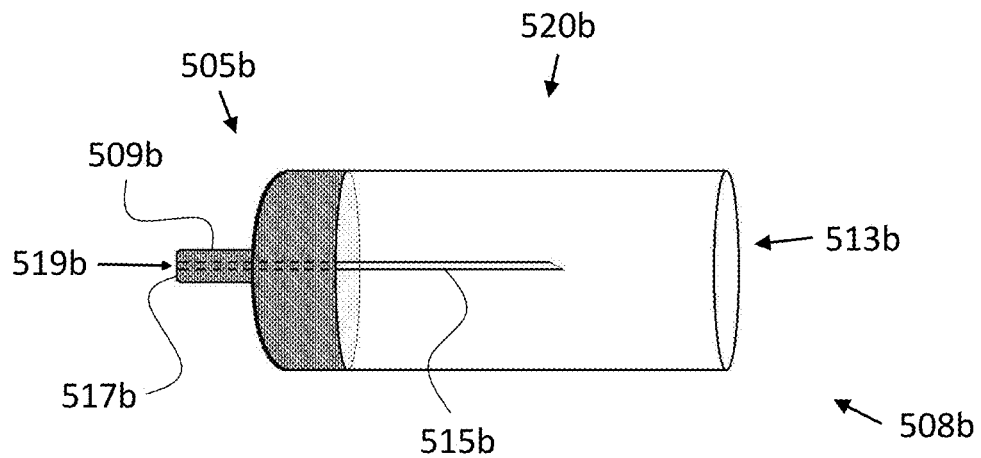
Figure 5C:
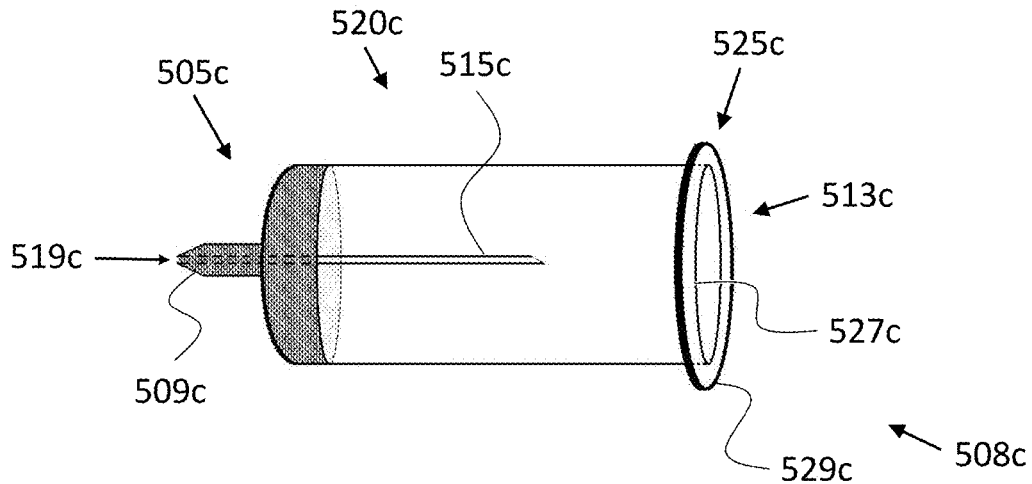
Figure 5D:
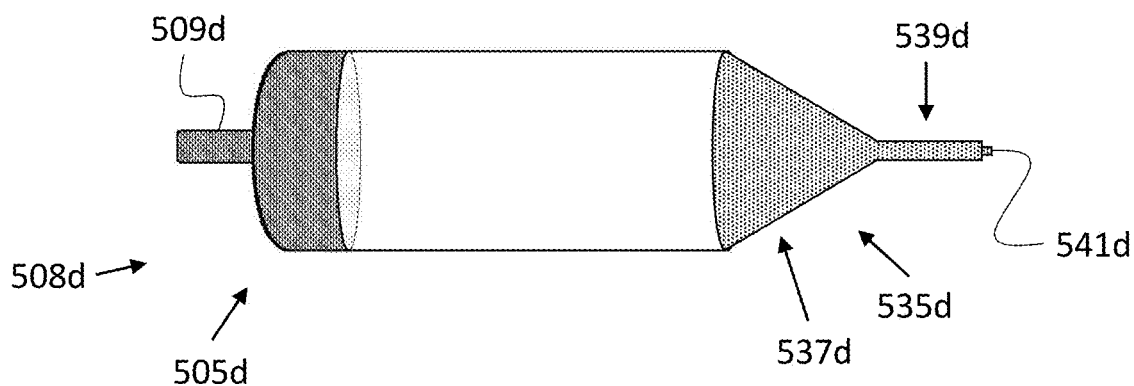

According to some embodiments, applicator 108 includes an electrically conducting collimator (not shown in FIGS. 1A and 1B), such as the collimator shown in FIG. 5D. The collimator may be mounted on a distal end 128 of applicator 108. The collimator is configured to induce the formation of a collimated (focused) plasma discharge (outside of applicator 108), essentially as explained in the descriptions of FIG. 5D and FIG. 8B.

Control unit 112 may include electronics configured to control and coordinate operation of components within handle 106. According to some embodiments, control unit 112 may be, or include, a microcontroller. In particular, control unit 112 is functionally associated with flyback amplifier 114. Electrical wires functionally associating control unit 112 with flyback amplifier 114, and flyback amplifier 114 with connector 116, are not shown.

According to some embodiments, and as depicted in FIG. 1A, handle 106 may include a user interface 132 functionally associated with control unit 112 and allowing a user (e.g. a dermatologist) of discharge device 102 to control the operation thereof. User interface 132 may include one or more buttons 132a (or knobs or switches, and the like) and/or at least one screen 132b. As a non-limiting example, three buttons are depicted in FIG. 1: an on/off button, a power increase button, and a power decrease button. In particular, the user interface may allow a user to switch on/off discharge device 102, and, optionally, to select a treatment program and/or set/adjust treatment parameters, such as the duration of a treatment, the amplitude of the voltage signal (applied at the cathode), the parameters characterizing the voltage signal (e.g. the shape of the pulses, the inter-pulse separation, and so on).

Screen 132b may constitute a graphical user interface configured to display to the user information related to the operation of discharge device 102, such as, for example, parameters relating to the operation of discharge device 102, which may include the treatment program selected, the time elapsed since the start of a treatment, the amplitude of the applied voltage, and so on. Optionally, according to some embodiments described below, wherein handle 106 includes a camera, the screen may be configured to additionally display images and/or videos captured by the camera of a treated site (during treatment). According to some embodiments, screen 132b may be a touch screen. According to some embodiments, the user interface may include a voice-user interface (and handle 106 may include a microphone) allowing a user to operate discharge device 102 by spoken commands.

According to some alternative embodiments, not depicted in FIG. 1A, the user interface may be external to handle 106, and may include, for example, a foot pedal, in place of buttons 132a, and/or an external screen in place of screen 132b. According to some embodiments, components related to functions (controllable by the user interface) may be included in handle 106 while other components related to other functions (controllable by the user interface) may be external to handle 106.

According to some embodiments, not depicted in FIGS. 1A and 1B, discharge device 102 may further include a thickness meter configured to measure a thickness of a target skin growth abnormality, as described below in the description of FIG. 2 and in the Methods subsection.

Control infrastructure 104 includes elements external to discharge device 102, which are related to the operation of discharge device 102. Control infrastructure 104 is delineated by a dashed-double-dotted line to indicate that the elements, listed as included therein, need not necessarily be housed in a single housing. Control infrastructure 104 may include a waveform generator 138 (e.g. an arbitrary waveform generator) and a main control unit 150. Optionally, according to some embodiments, control infrastructure 104 may further include a communication unit 156 configured for communication with external communication networks and server computers, as elaborated on below in the description of FIG. 2.

Elements (components) of control infrastructure 104 may be functionally associated with corresponding elements in handle 106 via electrical wires. Waveform generator 138 may be electrically coupled to flyback amplifier 114. Waveform generator 138 is configured to produce a controllably adjustable voltage signal, which is relayed to flyback amplifier 114 and amplified thereby. Main control unit 150 and control unit 112 may be communicatively associated by wire (e.g. by an electrical wire or an optical fiber) or wirelessly (e.g. by Bluetooth or Wi-Fi).

According to some embodiments, wherein the elements of control infrastructure 104 are housed within a single housing (i.e. an external controller), elements of control infrastructure 104 and elements of handle 106 may be functionally (and optionally communicatively) associated via a single utility cable 160. Utility cable 160 may include electrical wires and, optionally, at least one optical fiber.

According to some embodiments, utility cable 160 may be detachably connected to handle 106. According to some such embodiments, handle 106 may include, e.g. on a proximal end thereof, a plug 161 (shown in FIG. 1B) configured to be connected to a cable plug 163 on a distal end of utility cable 160. Electrical wires, and optionally one or more optical fibers (for example, in some embodiments wherein a camera is included in handle 106), extending from plug 161 to control unit 112, and, optionally, to other components within discharge device 102, are not shown. In particular, the electrical wires may include wires for powering discharge device 102. According to some embodiments, the electrical wires may further include a wire coupling one end of distal coil 124b to a ground anode (not shown) in control infrastructure 104 (the other end of distal coil 124b being electrically coupled to the cathode within applicator 108). Alternatively, according to some embodiments, one end of distal coil 124b may be left exposed, effectively functioning as the anode.

According to some embodiments, and as depicted in FIG. 1B, plug 161 may be a female plug including holes 165 for matching pins in cable plug 163, which is a male plug. Alternatively, plug 161 may be a male plug and cable plug 163 may be a matching female plug. Pairs of matching holes and pins may be configured to electrically couple corresponding electrical wires in handle 106 and utility cable 160. According to some embodiments, at least one pair of matching hole and pin may be configured to optically couple corresponding optical fibers in handle 106 and utility cable 160.

According to some embodiments, plug 161 and cable plug 163 may be mechanically secured to one another. According to some embodiments, plug 161 and cable plug 163 may be mechanically secured to one another via screw cap mechanism. For example, according to some embodiments, plug 161 may be threaded and cable plug 163 may include a screw cap, such as allow mechanically securing utility cable 160 onto handle 106. Other types of mechanical securing mechanisms are also possible, such as pin lock-based mechanisms and snap-engagement-based mechanisms.

According to some embodiments, control infrastructure 104 may be configured to be electrically connected to an external power source (e.g. a wall socket) in order to power operation thereof and of discharge device 102. According to some embodiments, control infrastructure 104 may include a battery for powering operation thereof and of discharge device 102. According to some embodiments, the battery may be rechargeable and/or replaceable.

Figure 2:
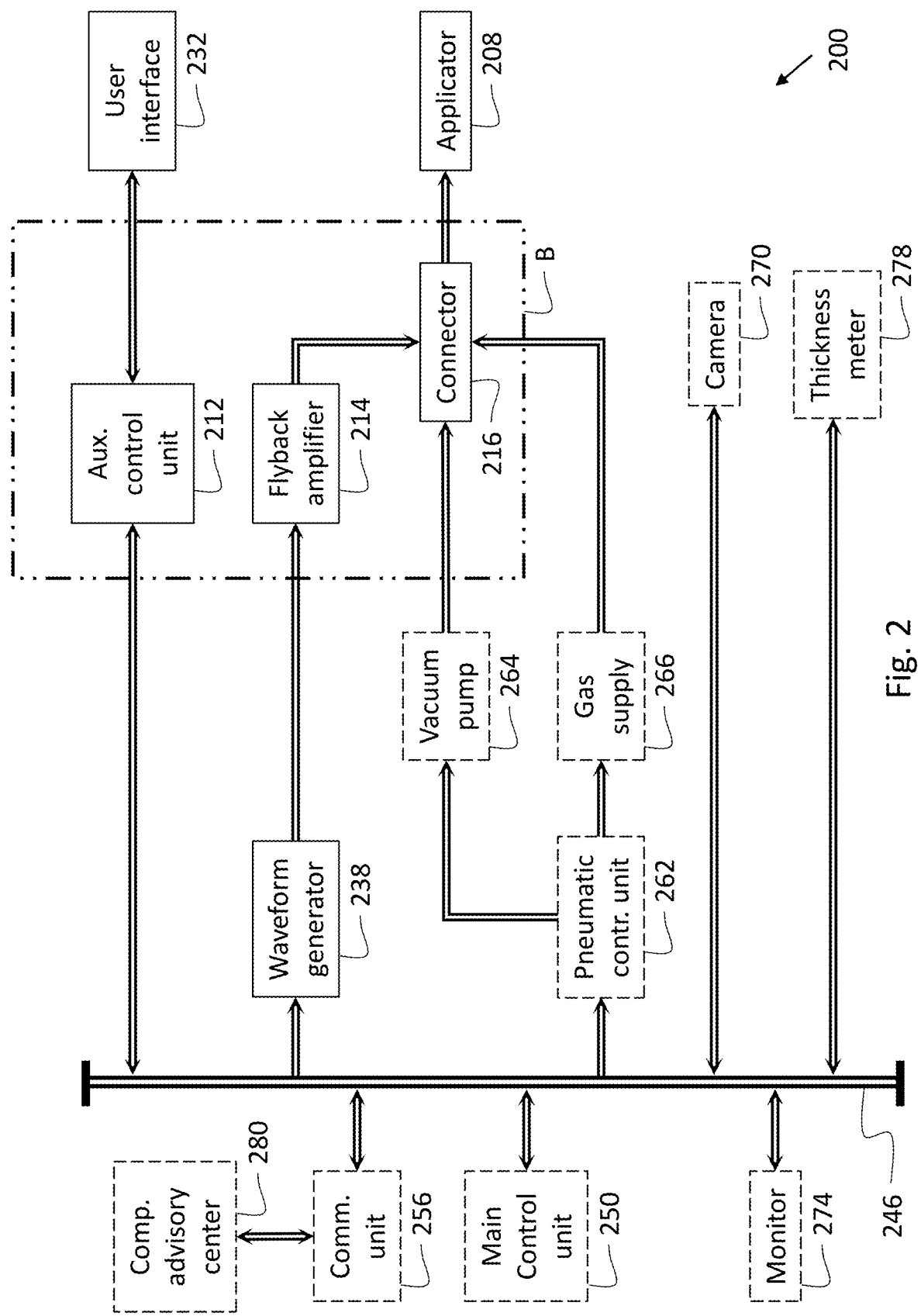
FIG. 2 is a block diagram of a system for treating skin tissue and nails using cold plasma, according to some embodiments.

FIG. 2 is a block diagram of a cold-plasma discharge system 200 for treatment of non-malignant skin growths and abnormalities, according to some embodiments. System 200 includes an applicator 208, a waveform generator 238 (i.e.

a function generator), a flyback amplifier 214, a connector 216, an (auxiliary) control unit 212, a computer bus 246, and a user interface 232. According to some embodiments, system 200 may include a cold-plasma discharge device, including a handle and applicator 208, and an external control infrastructure, which may be housed in an external controller connected to the discharge device via a utility cable, such as utility cable 160, or when pneumatic infrastructure is included, a utility cable such as described in the description of FIG. 3A.

Figure 4:
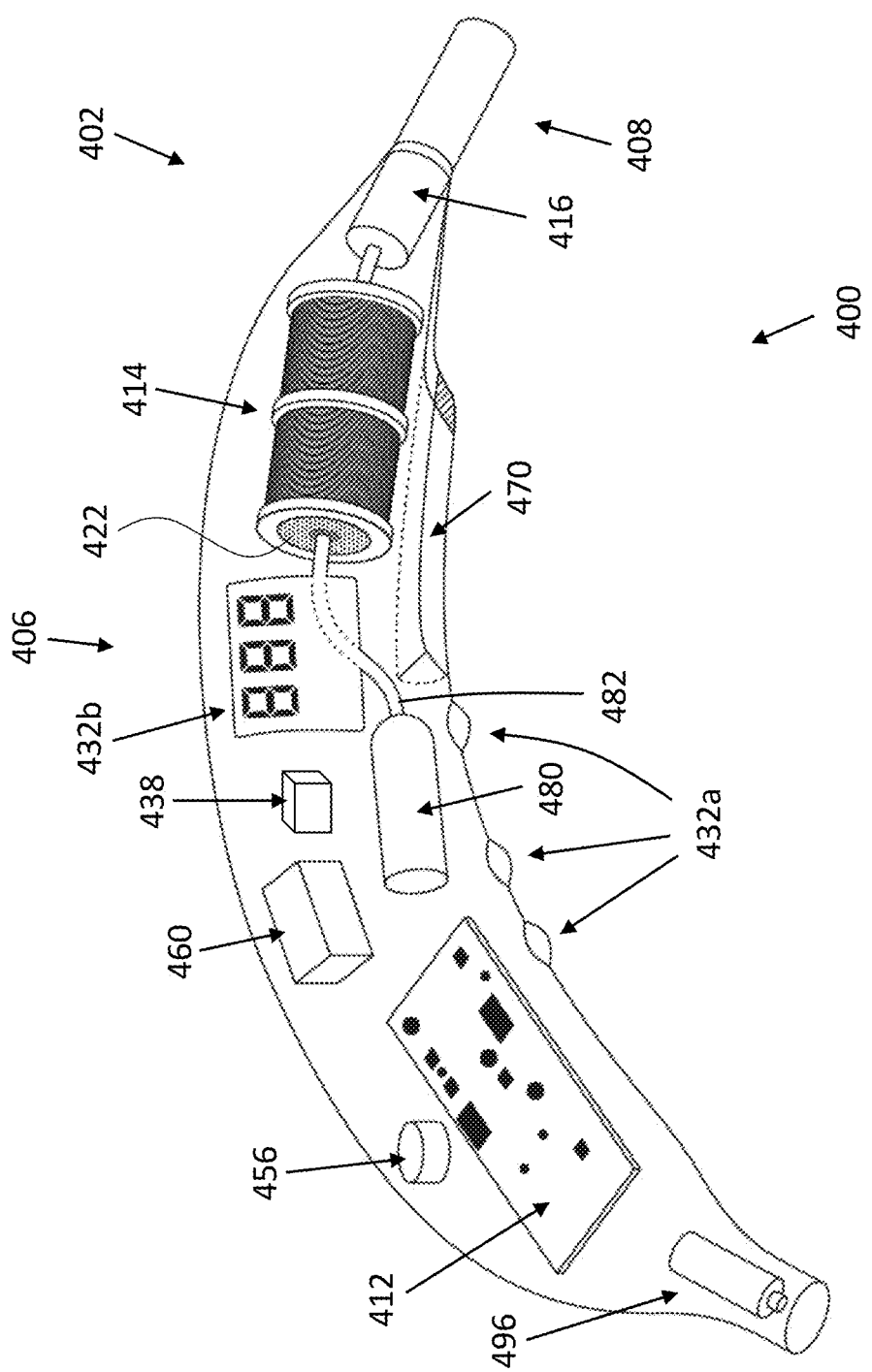
FIG. 4 schematically depicts a cold-plasma discharge device including a handle and a cold-plasma applicator, the discharge device constituting an autonomous system for treating skin tissue and nails using cold plasma, according to some embodiments.

Alternatively, according to some embodiments, such as described, for example, in the description of FIG. 4, the discharge device may be autonomous in the sense of including all of the components of system 200. In particular, in such embodiments, the discharge device is configured to perform the full range of functions of system 200 (without requiring any external control infrastructure). Further, according to some such embodiments, wherein the discharge device is self-powered, i.e. including a battery, the anode of the plasma discharge "circuit" may be positioned on the handle (on a position thereon whereon the handle is held by an operator) or configured to be placed on the skin of the subject (e.g. near the target site). In the latter embodiments, an electrical cable terminating in the anode may extend outside the handle, and the anode may be in the form of a patch electrode configured for placement on a skin surface.

Applicator 208 may be mounted on a distal tip portion of the handle, essentially as depicted in FIGS. 1A and 1B and FIGS. 3A-4.

Figure 3A:
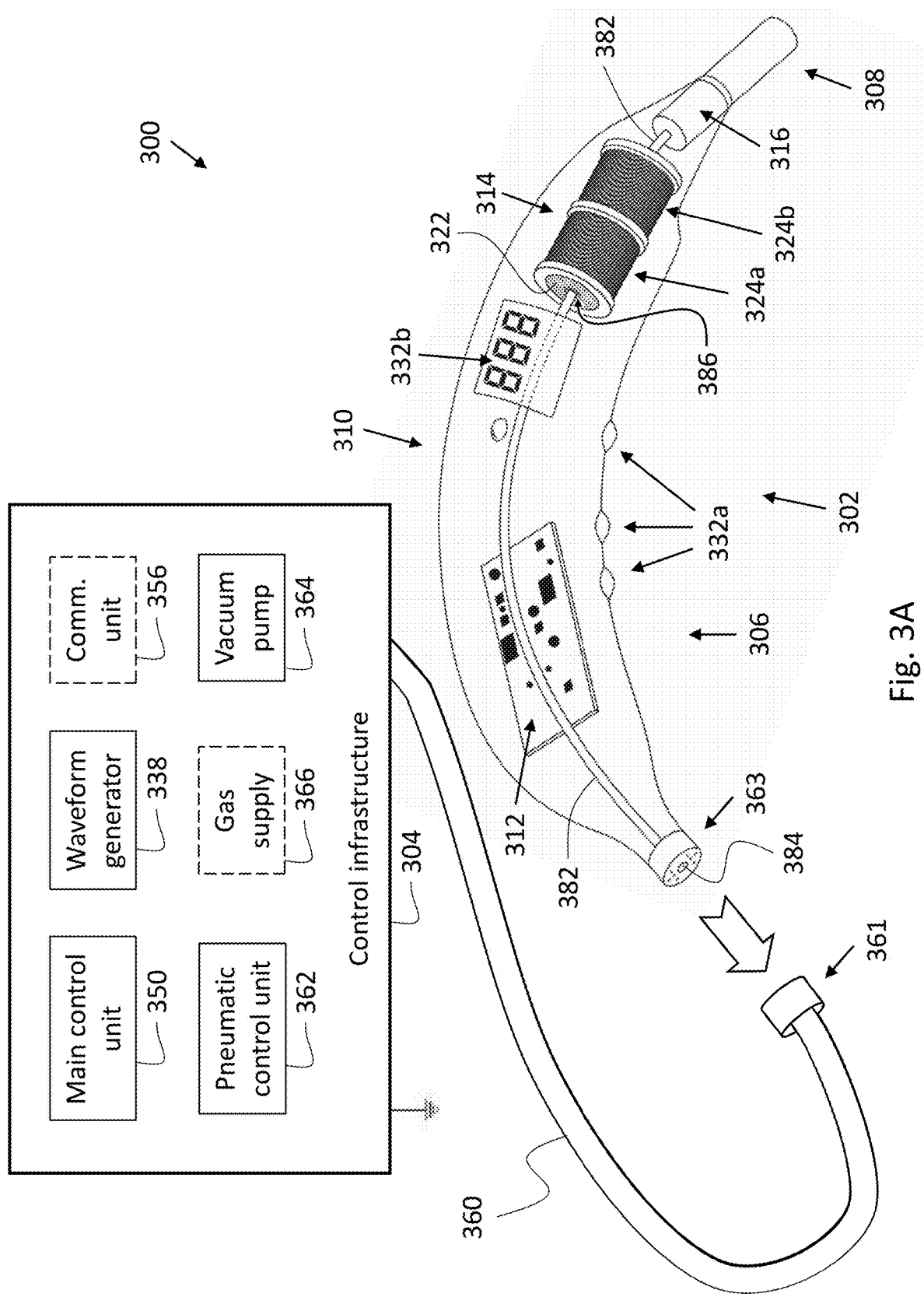
FIG. 3A schematically depicts a system for treating skin tissue and nails using cold plasma, the system includes a cold-plasma discharge device and external control infrastructure, the discharge device includes a handle and a cold-plasma applicator, the system includes pneumatic infrastructure for controlling gas-pressure within the cold-plasma applicator, according to some embodiments.

Flyback amplifier 214, connector 216, and control unit 212 are shown enclosed within a dashed-double-dotted box B to indicate that flyback amplifier 214, connector 216, and control unit 212 are typically housed within a common housing, such as housing 110 of handle 106, each of the housings of the handles depicted in FIGS. 3A-4, and housings of handles similar thereto.

System 100 constitutes a specific embodiment of system 200.

Applicator 208 may include a closed tube or an open-ended tube (on the distal end thereof), according to whether the cathode directly or indirectly ionizes ambient air about a treatment site on the skin (such as to produce a cold-plasma discharge directed at the treatment site). A cap cathode (i.e. an electrode in the form of a cap) may be mounted on a proximal portion of the tube. According to some embodiments, the cap cathode may include a needle extending into the tube.

More specifically, in embodiments wherein applicator 208 includes a closed tube (e.g. a capsule, as depicted, for example, in FIGS. 5A, 5B, 5D, and 5E), the tube may include an inert gas (e.g. neon and/or argon) and/or air at sub-atmospheric pressure of at least about 2 kPa or higher. In embodiments wherein the distal end of applicator 208 is open-ended (as depicted, for example, in FIG. 5C), the distal end of the tube may be configured to be placed on the skin of a subject, such as to surround a treatment site and, optionally, form a fluidly-sealed, or a substantially fluidly-sealed environment. The fluidly-sealed environment may be controllably depressurized to (sub-atmospheric) pressures of at least about 2 kPa or higher.

As used herein, the term "closed tube" may be used to refer to a tube, such as a capsule. That is, a tube which is fluidly-sealed except, optionally, including a gas port (or gas inlet) on a proximal portion thereof, which allows for controllable introduction of gas into the tube or withdrawal of gas from the tube.

Connector 216 is electrically coupled to flyback amplifier 214. Applicator 208 is mounted on, or configured to be detachably mounted on, connector 216, such that the cathode in applicator 208 is electrically coupled to flyback amplifier 214 (via connector 216). Flyback amplifier 214 is electrically coupled to waveform generator 238 and is configured to amplify the amplitude of a voltage signal produced by waveform generator 238, such as to produce a voltage at the cathode having an amplitude greater than about 10 kV. According to some embodiments, flyback amplifier 214 may be a step-up transformer.

Waveform generator 238 is configured to be electrically coupled to an electric power source and may be further configured to produce an oscillating (input) voltage signal. According to some embodiments, the input voltage signal may be pulsed, thereby producing a series of (voltage) pulses at the cathode. The series of pulses (applied at the cathode) may be characterized by one or more frequencies ranging from about 10 kHz to about 1 GHz. More generally, each pulse may have a frequency spectrum between about 10 kHz and about 1 GHz.

According to some embodiments, the pulses may be characterized by a single frequency, may be (amplitude) modulated or double-modulated, or may be harmonic. According to some embodiments, each pulse may be modulated by a monotonically decreasing function. According to some embodiments, the monotonically decaying function may be an exponentially decaying function, or substantially exponentially decaying function, or a hyperbolic decaying function, or substantially hyperbolic decaying function. According to some embodiments, the monotonically decreasing function may include a first segment, which may be flat or slowly decaying, followed by a second segment which is sharply decreasing.

According to some embodiments, the pulses may be characterized by varying duty cycles (power cycles). That is to say, pulse width and/or inter-pulse separation may vary from one pulse to the next. According to some embodiments, the pulse widths may range from about 10 nsec (i.e. nanoseconds) to about 200 nsec, from about 10 nsec to about 100 nsec, or from about 20 nsec to about 80 nsec. Each possibility corresponds to different embodiments. According to some embodiments, the pulse widths may measure about 50 nsec.

According to some embodiments, the duty cycle of the series of pulses may be selected such that the power of the plasma beam incident on the treatment site is on the order of 1 μW (e.g. between 0.1 μW and 10 μW). According to some embodiments, the duty cycle may be between about 1% and about 70% of the total cycle. In some embodiments, the duty cycle may be between about 5% and about 65% of the total cycle. In some embodiments, the duty cycle may be between about 10% and about 60% of the total cycle. In some embodiments, the duty cycle may be between about 15% and about 55% of the total cycle. In some embodiments, the duty cycle may be between about 20% and about 50% of the total cycle. Each possibility corresponds to separate embodiments.

According to some embodiments, the electrical power source may be an alternating current (AC) power source, for example, when the electricity is supplied via a wall outlet. According to some embodiments, the electrical power source may be a direct current (DC) power source, for example, when the power source is a battery.

Waveform generator 238 may include a periodic signal generator and a signal modulator. The periodic signal generator may be configured to convert a supplied voltage signal, into a periodic voltage signal—such as a sine voltage signal, square-wave voltage signal, or a sawtooth voltage signal—of a desired frequency. The signal modulator may be configured to modulate the amplitude of the envelope of the periodic voltage signal.

Computer bus 246 is configured to communicatively and functionally associated with different elements of system 200.

According to some embodiments, system 200 further includes pneumatic infrastructure including a pneumatic control unit 262 and a vacuum pump 264 and/or a gas supply 266. Additional components—such as a valve system for guiding gas from gas supply 266 to applicator 208, an injection head, a pressure sensor configured to measure the gas pressure within applicator 208, and, optionally, a gas mixer—are not shown. According to some embodiments, the valve system may include electronic valves. Pneumatic control unit 262 may be configured to control and coordinate operation of the valve system, vacuum pump 264, and gas supply 266. To this end, pneumatic control unit 262 may include suitable electronic and mechanical components.

Pneumatic control unit 262 may be functionally associated with control unit 212 and/or a main control unit (in embodiments wherein system 200 includes external control infrastructure, as described below), which may be configured to control the operation thereof. In embodiments including vacuum pump 264, the pneumatic infrastructure may be utilized to reduce the pressure within applicator 208 to a desired (sub-atmospheric pressure) level and maintain the pressure at the desired level. In embodiments including the gas mixer, the gas mixer may be used to ensure that different types of gases present within applicator 208 are homogeneously distributed therewithin (i.e. that the gases are well mixed). In particular, the gas mixer may be employed when changing the composition of gases within applicator 208 as follows: Gas from applicator 208 may be withdrawn to the gas mixer, wherein the gas from the applicator 208 may be mixed with second gas from gas supply 266. The resulting homogenous mixture of gases may then be pumped into applicator 208.

According to some embodiments, system 200 may further include a camera 270 (e.g. a visible-light camera) configured to capture photos and videos of a treatment site during treatment, essentially as described below in the Methods subsection. According to some embodiments, camera 270 may be an infrared camera or additionally include thermal imaging capabilities. According to some embodiments, camera 270 may be used to monitor in real-time the temperature of the plasma discharge.

According to some embodiments, system 200 may further include monitor 274, which may be included in the external control infrastructure. Monitor 274 may be configured to display images captured by camera 270. According to some embodiments, monitor 274 may be configured to play video captured by camera 270, optionally, in real-time.

According to some embodiments, system 200 may further include a thickness meter 278 configured to measure the thickness of a target skin growth/abnormality (both when a skin growth/abnormality is at least partially ingrown and when the skin growth/abnormality protrudes from surrounding skin surface). According to some embodiments, thickness meter 278 may be an external ultrasound probe. According to some such embodiments, measurement data of the ultrasound probe may be used to generate ultrasound images of the target skin growth/abnormality.

Figure 3B:
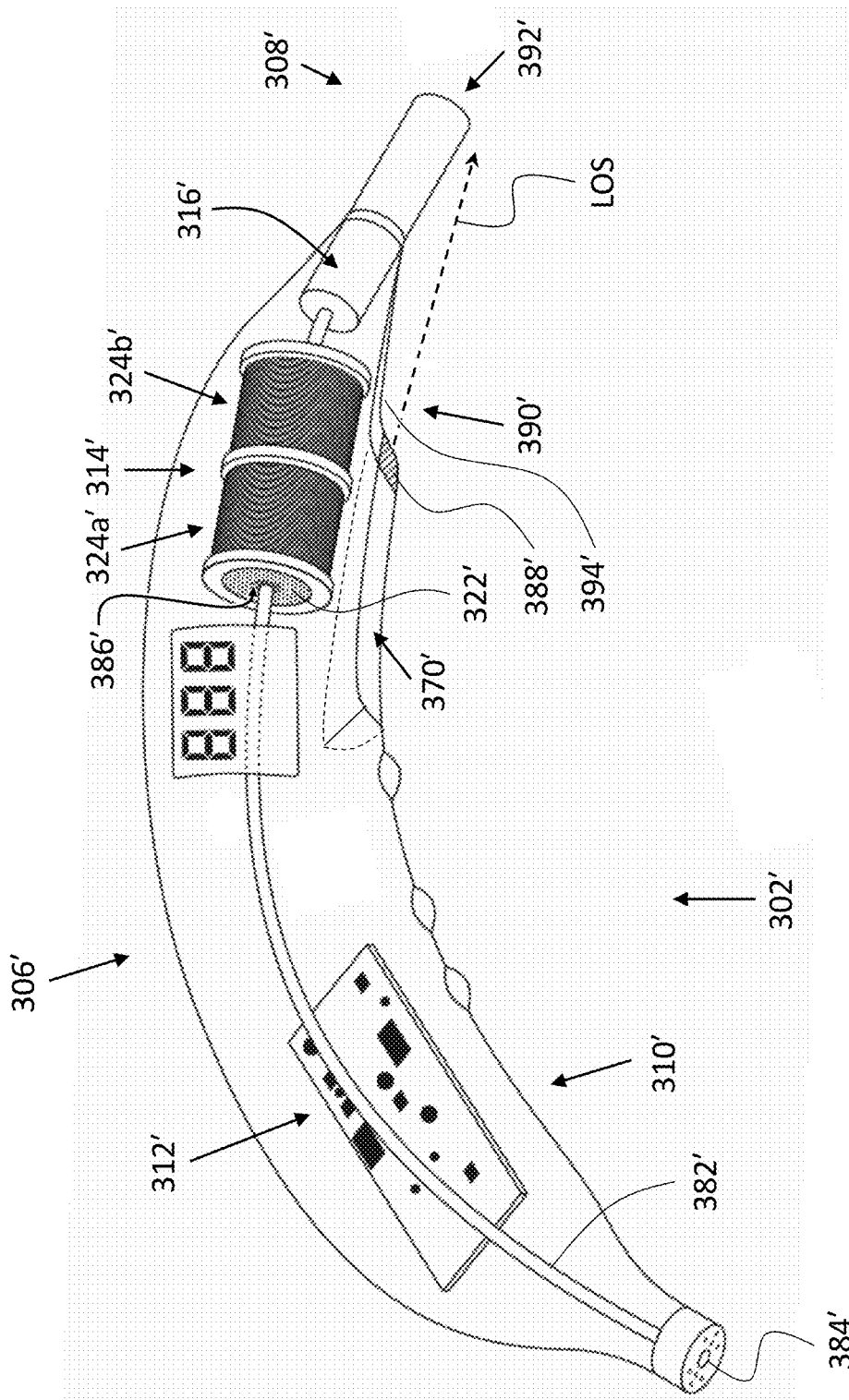
FIG. 3B schematically depicts a cold-plasma discharge device, which is a specific embodiment of the discharge device of FIG. 3A.

According to some embodiments, wherein system 200 includes external control infrastructure, such as, for example, control infrastructure 104 of system 100 or the control infrastructures of the systems of FIGS. 3A and 3B, system 200 may further include a main control unit 250. Main control unit 250 may include one or more processors and volatile and non-volatile memory components. Main control unit 250 is configured to control and coordinate the operation of elements included in the control infrastructure. Main control unit 250 may further be configured to coordinate between the operation of elements of the control infrastructure and the operation of elements within the discharge device (e.g. discharge device 102 or the discharge devices of FIGS. 3A and 3B). In particular, main control unit 250 may be communicatively associated with control unit 212 via computer bus 246. According to some embodiments, main control unit 250 may be configured to command control unit 212.

According to some embodiments, system 200 may further include a communication unit 256 configured to communicatively associate with external communication networks (i.e. the internet), server computers, and local computer networks (e.g. a hospital computer network). According to some embodiments, communication unit 256 may be a wireless communication unit configured to (i) apply wireless communication protocols, such as Wi-Fi, ZigBee, Bluetooth, and/or (ii) connect to a wireless local area network (LAN), and/or (iii) a mobile (cellular) network (e.g. when the discharge device is autonomous).

System 200 may be communicatively associated (via communication unit 256) with a computerized advisory center 280, which may be cloud-based. The advisory center may include a treatment database, a treatment analysis module, and a treatment advisory module. The treatment analysis module and the treatment advisory module may be implemented by one or more processors in one or more server computers. The treatment database may be stored in a cloud storage (of the one or more server computers or associated therewith).

The treatment database may include data collected during treatments performed using system 200. The collected data may include: (i) the type of skin growth/abnormality or nail disorder, as well as characterizing features thereof such as the thickness thereof or even the shape thereof (which may be obtained e.g. from ultrasound images of the skin growth/abnormality), and the location thereof on the body (e.g. on the arm or the face); (ii) treatment parameters, such as the applicator used, parameters specifying the voltage signal, the type/composition of gas used, the gas pressure, and the duration of the treatment; (iii) images and video captured during the treatment; and (iv) treatment results (i.e. the success of the treatment, the healing time, whether a scar has formed, and whether the treatment had to be repeated). The collected data may also include personal data of a subject, such as age and gender, as well as "subjective data", such as whether the subject experienced any discomfort during the treatment.

For the purposes of identifying the type of skin growth/abnormality or nail disorder, the advisory center may be communicatively associated with an external dermatological database including a searchable atlas of skin growths and abnormalities and/or nail disorders.

The treatment analysis module may be configured to detect successful treatment patterns in past treatments data (i.e. the data of past treatments) stored in the treatment database. That is to say, the treatment analysis module may be configured to analyze past treatments data to identify—per each type of skin growth/abnormality (or nail disorder)—optimal, or substantially optimal, treatment parameters. According to some embodiments, the treatment analysis module may be configured to optimally, or substantially optimally, partition the subjects—per each type of skin growth/abnormality (or nail disorder)—into subject classes (populations), such that, per each subject class, optimal, or substantially optimal, treatment parameters are identified. Subject classes may be characterized by one or more of, for example, age group, gender, weight category, and common medical conditions.

To identify successful treatment patterns, the treatment analysis module may utilize big data analytics tools, machine-learning tools, and, more generally, artificial intelligence (AI) based tools.

The treatment advisory module may be configured to prescribe a treatment to a subject based on subject data, such as the age, gender, weight, and/or medical history thereof, and the analysis of past treatments by the treatment analysis module. According to some embodiments, wherein a treatment to be undergone by a subject is not the first treatment undergone by the subject using the disclosed devices and methods, the treatment advisory module may be configured to take into account data from past treatments of the subject in prescribing the current treatment to be undergone the subject. In particular, according to some embodiments, a subject may be an outlier relative to other subjects in a same subject class, in the sense that the subject reacts significantly differently and non-optimally, or even negatively, to the optimal treatments assigned to the subject class. The treatment advisory module may be configured to identify outlier subjects based on past treatment data thereof and to discount the subject class in prescribing the treatment to the subject.

To prescribe a treatment to a subject, the treatment analysis module may utilize artificial intelligence (AI) based tools, such as artificial neural networks.

According to some embodiments, there may be two separate computerized advisory centers, one for dermatological treatments and one for cosmetic treatments. According to some embodiments, the computerized advisory center for dermatological treatments may include a computerized advisory sub-center for skin conditions and abnormalities and a computerized advisory sub-center for nail diseases and disorders.

According to some alternative embodiments, flyback amplifier 214 may include a piezoelectric crystal electrically coupled on a first end thereof to the cathode (in applicator 208) and on a second end thereof to an anode (which may function, or effectively function, as a ground terminal) in the control infrastructure. In such embodiments, waveform generator 238 may be mechanically coupled to the piezoelectric crystal, such as to generate controllable stress vibrations in the piezoelectric crystal, which in turn induce a voltage (potential difference) between the applicator cathode and the anode.

FIG. 3A schematically depicts a cold-plasma discharge system 300 for treatment of non-malignant skin growths and abnormalities, according to some embodiments. System 300 includes a cold-plasma discharge device 302 and external control infrastructure 304. Discharge device 302 includes a handle 306 and a cold-plasma applicator 308. An outline of a housing 310 of handle 306 is indicated but otherwise housing 310 is depicted as transparent so as to render visible components included therein. System 300 differs from system 100 at least in including pneumatic infrastructure for controlling the gas pressure within applicator 308 but may otherwise be essentially similar thereto.

In particular, handle 306 differs from handle 106 in including a gas duct 382 (i.e. a gas pipe) and an injection head (not shown) configured for injecting gas into and/or withdrawing gas from applicator 308. According to some embodiments, gas duct 382 may extend in the distal direction from a plug gas port 384 (i.e. a gas port 384 on a plug 361 positioned on a proximal end of handle 306) to the injection head. According to some embodiments, applicator 308 differs from applicator 108 at least in including an applicator gas port (a gas port of the applicator; not shown). In such embodiments, unlike applicator 108 (which includes tube 120, which is permanently fluidly-sealed without option of withdrawing therefrom or introducing gas thereinto), applicator 308 may allow changing the composition and the pressure of gas included therein, as elaborated on below.

It is, however, to be understood that the inclusion of gas duct 382 and related pneumatic components (e.g. the injection head and plug gas port 384) in handle 306—according to some embodiments—does not preclude the possibility of mounting on handle 306 an applicator, which includes a permanently fluidly-sealed tube, such as applicator 108 (i.e. a tube which does not allow introduction of gas thereinto or withdrawal of gas therefrom).

More specifically, handle 306 includes an (auxiliary) control unit 312, a flyback amplifier 314, and a connector 316. Control unit 312 may include processing and memory circuitry, or alternatively even more rudimentary electronic circuits, configured to control and coordinate operation of components within handle 306. According to some embodiments, control unit 312 may be or include a microcontroller. In particular, control unit 312 is functionally associated with flyback amplifier 314. Electrical wires functionally associating control unit 312 with flyback amplifier 314, and flyback amplifier 314 with connector 316, are not shown.

Control unit 312 may further be configured to control operation and coordinate operation of pneumatic components within handle 306, in particular, the injection head—which, according to some embodiments, may be included in connector 316—and plug gas port 384. According to some embodiments, a core 322 of flyback amplifier 314 includes a central core drilling 386 extending from the proximal end of core 322 to the distal end of core 322. Also indicated are a proximal coil 324a and a distal coil 324b of flyback amplifier 314. Gas duct 382 extends through core 322 onto the injection head in connector 316.

Connector 316 may be configured to (i) mechanically secure applicator 308 to handle 306, (ii) electrically couple applicator 308 to flyback amplifier 314, and (iii) fluidly couple applicator 308 to gas duct 382.

Control infrastructure 304 includes a main control unit 350, a waveform generator 338, and, optionally, a communication unit 356, which are specific embodiments, of main control unit 250, waveform generator 238, and communication unit 256 of system 200. Control infrastructure 304 further includes a pneumatic control unit 362, a vacuum pump 364, and, optionally, a gas supply 366, which are specific embodiments of pneumatic control unit 262, vacuum pump 264, and, optionally, gas supply 266 of system 200.

According to some embodiments, wherein the elements of control infrastructure 104 are housed within a single housing, elements of control infrastructure 304 and elements of handle 306 may be functionally (and optionally communicatively) associated via a single utility cable 360, which is configured to be connected to plug 361 (via a cable plug 363 of utility cable 360). Utility cable 360 differs from utility cable 160 at least in additionally including a gas duct configured to be fluidly coupled, via plug gas port 384, to gas duct 382.

Also indicated in FIG. 3A are one or more buttons 332a and a screen 332b of a user interface 332.

FIG. 3B schematically depicts a cold-plasma discharge device 302' for treatment of non-malignant skin growths and abnormalities, according to some embodiments. Discharge device 302' constitutes a specific embodiment of discharge device 302. Discharge device includes a handle 306' and a cold-plasma applicator 308', which are specific embodiments of handle 306 and cold-plasma applicator 308, respectively. An outline of a housing 310' of handle 306' is indicated but otherwise housing 310' is depicted as transparent so as to render visible components included therein.

Handle 306' includes an (auxiliary) control unit 312', a flyback amplifier 314', a connector 316', and a gas duct 382', which are specific embodiments of control unit 312, flyback amplifier 314, connector 316, and gas duct 382, respectively, of handle 306. Handle 306' additionally includes a camera 370'. A lens 388' of camera 370' is positioned on a distal section 390' of handle 306' at a line-of-sight LOS from a (distal) applicator tip 392' (i.e. the distal tip of applicator 308'). Camera 370' is thereby configured to capture images, video, and/or a heat map of a treated site during treatment, and, optionally, the plasma discharge beam. More specifically, a bottom surface 394' of distal section 390' may be "chipped" (i.e. inclined at a sufficiently sharp angle) such as to provide camera 370' with a view of applicator tip 392'.

Also indicated is a core 322', a proximal coil 324a', a distal coil 324b', and a central core drilling 386' of flyback amplifier 314', as well as a plug gas port 384'.

According to some embodiments, discharge device 302' is configured to be used in conjunction with external control infrastructure (not shown in FIG. 3B), which may include a monitor configured to display images and/or video obtained by camera 370'.

According to some embodiments, the monitor may be configured to display ultrasound images obtained by an external ultrasound probe. The control infrastructure may be a specific embodiment of control infrastructure 304.

FIG. 4 schematically depicts a cold-plasma discharge device 402, according to some embodiments. Discharge device 402 constitutes an autonomous cold-plasma discharge system 400 for treatment of non-malignant skin growths and abnormalities. Discharge device 402 is said to be autonomous in the sense of not being reliant on, and not requiring, external control infrastructure in order to operate in full. In other words, all components of system 400 are included within discharge device 402. In particular, system 400 constitutes a specific embodiment of system 200, wherein specific embodiments of all non-optional elements of system 200 are included in discharge device 402. It is to be understood that in embodiments wherein system 400 further includes one or more specific embodiments of optional elements of system 200, these too are included in discharge device 402.

Discharge device 402 includes a handle 406 and an applicator 408 mounted thereon. An outline of a housing 410 of handle 406 is indicated but otherwise housing 410 is depicted as transparent so as to render visible components included therein. More specifically, handle 406 a flyback amplifier 414, a connector 416, and a waveform generator 438, which are specific embodiments of flyback amplifier 214, connector 216, and waveform generator 238, respectively. Control unit 412 may include electronics configured to control and coordinate operation of components within handle 406. According to some embodiments, control unit 412 may be or include a microcontroller. It is noted that since all of the control infrastructure is included within discharge device 402, control unit 412 may combine functions of both main control unit 250 and auxiliary control unit 212 of system 200. In particular, control unit 412 is functionally associated with waveform generator 438, flyback amplifier 414, and a pneumatic control unit 460 (described below). Electrical wires functionally associating control unit 412 with waveform generator 438, waveform generator 438 with flyback amplifier 414, and flyback amplifier 414 with connector 416, and, optionally, control unit 412 with pneumatic control unit 460, are not shown.

The distal coil (not numbered) of flyback amplifier 414 is electrically coupled to the one on end thereof to the cathode (in applicator 408). The second end of the distal coil may be left exposed. (In such embodiments, the second end of the distal coil constitutes the anode.) Alternatively, the second of the distal coil may be coupled to an anode on housing 410.

Handle 406 further includes pneumatic infrastructure including a container 480, a gas duct 482, and an injection head (not shown) positioned in connector 416 and configured for injecting gas into and/or withdrawing gas from applicator 408. More specifically, gas duct 482 extends, via a ferromagnetic core 422 of flyback amplifier 414, from a proximal end of gas duct 482, which is connected to container 480, to a distal end of gas duct 482, which is connected to the injection head.

According to some embodiments, container 480 may include a vacuum pump (not shown) and a first compartment. The vacuum pump may be configured to withdraw gas from applicator 408, which may be evicted into the first compartment. According to some embodiments, container 480 may further include a second compartment (i.e. a gas supply) storing an inert gas (which may be compressed). The second compartment may include valve, which when open fluidly couples the second compartment to applicator 408, thereby allowing for flow of gas from the second compartment (via gas duct 482) into applicator 408. According to some embodiments, container 480 may further include a gas mixer (not shown).

Pneumatic control unit 460 is configured to control operation and coordinate operation of the pneumatic components (i.e. the vacuum pump, the injection head, etc.) within handle 406. According to some embodiments, pneumatic control unit 460 is configured to be commanded by control unit 412.

According to some embodiments, discharge device 402 may be cordless, including a battery 496 configured to power discharge device 402 operation. According to some embodiments, battery 496 may be rechargeable and/or replaceable.

According to some embodiments, discharge device 402 may include a wireless communication unit 456, which is a specific embodiment of communication unit 256. Wireless communication unit 456 is configured to communicatively associate a control unit 412 of discharge device 402 with external communication networks and server computers.

According to some embodiments, discharge device 402 further includes a camera 470.

Also indicated is a user interface 432 including one or more buttons 432a and a screen 432b. FIGS. 5A-5E schematically depicts five different applicators for cold-plasma discharge devices, which are intended for treatment of non-malignant skin growths and abnormalities, according to some embodiments. Each of the depicted applicators constitutes a respective specific embodiment of applicator 208.

The applicators depicted in FIGS. 5A, 5B, 5D, and 5E, according to some embodiments thereof, may also be configured for treating nail diseases and disorders.

Referring to FIG. 5A, an applicator 508a is depicted, according to some embodiments. According to some embodiments, applicator 508a may be configured for the treatment of skin diseases and disorders. Applicator 508a includes an elongated closed tube 520a, and a cap cathode 505a. Cap cathode 505a is mounted on a proximal portion 507a of closed tube 520a and is configured to be mechanically secured (e.g. by a screw-based mechanism or a snap-engagement mechanism) and electrically connected to a corresponding connector, i.e. a corresponding embodiment of connector 216. More specifically, cap cathode 505a includes an electrical connection member 509a configured to electrically connect cap cathode 505a to the connector when cap cathode 505a (and therefore applicator 508a) is properly secured to the connector.

According to some embodiments, cap cathode 505a may be coated by a thin insulating layer, thereby facilitating the generation of a uniform dielectric barrier discharge (DBD).

According to some embodiments, and as depicted in FIG. 5A, electrical connection member 509a may be a male member (e.g. a plug) and the corresponding connector may include a matching female member (e.g. a socket). Alternatively, according to some embodiments, not depicted in FIG. 5A, electrical connection member 509a may be a female member and the corresponding connector may include a matching male member. As a non-limiting example, in FIG. 5A electrical connection member 509a is depicted as a (projecting) plug.

Cap cathode 505a is electrically conductive and may be made of a metal suitable for plasma discharge, as known in the art of plasma discharge (e.g. an inert and stable metal). According to some embodiments, cap cathode 505a may be made of copper or a metal including copper. The connector is configured to electrically couple cap cathode 505a to a flyback amplifier, such as, for example, flyback amplifier 114 in embodiments wherein applicator 508a is a specific embodiment of applicator 108 and may therefore be fitted on handle 106.

Closed tube 520a may be made of an electrically insulating material. According to some embodiments, closed tube 520a may be made of an electrically insulating vitreous material, such as glass or quartz. According to some embodiments, closed tube 520a may be configured to accommodate an inert gas (such as neon or argon), air, or a mixture thereof, at sub-atmospheric pressures of at least about 2 kPa or higher. According to some embodiments, a tube distal end 513a (i.e. a distal end of closed tube 520a) may constitute a flat surface (as depicted in FIG. 5A), a concave surface, or a corrugated surface, or may otherwise adapted to the dimensions, shape, and/or texture of a skin growth/abnormality. For example, a closed tube with a concave distal surface may be used for a skin growth protruding from a substantially flat skin surface, such as, an external wart. An example, wherein a more complex shape of the distal surface may be required, is a skin growth protruding from an interdigital fold.

According to embodiments, when applicator 508a is properly mounted on the connector, cap cathode 505a may be fully encompassed (covered) by the connector.

According to some embodiments, closed tube 520a is permanently fluidly-sealed, and applicator 508a constitutes a specific embodiment of applicator 108. In such embodiments, applicator 508a may be configured to be mounted on a connector, such as connector 116, or, more specifically, a connector of a handle which does not include any pneumatic infrastructure (and, in particular, does not include a gas duct extending therethrough).

According to some embodiments, closed tube 520a may include on a proximal surface thereof a gas inlet (not shown). Electrical connection member 509a may include a corresponding gas port (not shown) configured to be fluidly-connected on a distal end thereof to the gas-inlet, and on a proximal end thereof to an injection head in a connecter in a corresponding handle, thereby allowing to controllably fluidly-couple closed tube 520a to a gas duct in the handle. According to some such embodiments, applicator 508a may constitute a specific embodiment of applicator 308, applicator 308', or applicator 408, being thereby configured to be mounted on handle 306, handle 306', or handle 406, respectively.

Referring to FIG. 5B, an applicator 508b, including a closed tube 520b and a cap cathode 505b, is depicted, according to some embodiments. According to some embodiments, applicator 508b may be configured for skin rejuvenation, drying, and ozone therapy. Applicator 508b differs from applicator 508a in that cap cathode 505b further includes a hollow needle member 515b extending into closed tube 520b. Apart from needle member 515b, applicator 508b may otherwise be essentially similar to applicator 508a (according to some embodiments of applicator 508a). According to some embodiments, and as depicted in FIG. 5B, needle member 515b may be hollow, extending in the proximal direction to a proximal end 517b of electrical connection member 509b, such as to define an applicator gas port 519b (i.e. a gas port of applicator 508b) on proximal end 517b. Needle member 515b may be configured to allow withdrawal therethrough of gas from closed tube 520b, as well as injection therethrough of gas into closed tube 520b. Applicator 508b is thus configured to allow controlling the gas composition and pressure within closed tube 520b. Closed tube 520b may be configured to accommodate an inert gas (such as neon or argon), air, or a mixture thereof. According to some such embodiments, applicator 508b may constitute a specific embodiment of applicator 308, applicator 308', or applicator 408, being thereby configured to be mounted on handle 306, handle 306', or handle 406, respectively.

Needle member 515b may be metallic. In such embodiments, needle member 515b may be adapted for producing a corona discharge or spark (when a voltage is applied at cap cathode 505b), thereby facilitating the generation of a plasma discharge at lower levels of the applied voltage.

Also indicated in FIG. 5B is a tube distal end 513b, which may be similar to tube distal end 513a of applicator 508a.

Referring to FIG. 5C, an applicator 508c is depicted, according to some embodiments. According to some embodiments, applicator 508c may be configured for treatment of warts by desiccation (and, optionally, ablation). In particular, it is noted that applicator 508c may be configured to perform desiccation at skin temperature (i.e. without heating the skin at and around a target site). A filter may be placed in the front of the suction (e.g. in applicator gas port 519c) in order to eliminate contamination of components internal to applicator 508c and the handle. Applicator 508c differs from applicator 508b in including an open-ended tube 520c in place of closed tube 520b but may otherwise be similar to applicator 508b. More specifically, only a tube distal end 513c (a distal end of tube 520c) is open. According to some embodiments, tube distal end 513c may be in the form of a flange 525c radially extending from an inner rim 527c of open-ended tube 520c (and flange 525c).

As used herein, according to some embodiments, the term "open-ended tube" may be used to refer to a tube which is open only on one of the ends thereof (but which may nevertheless include a gas inlet on the other end).

According to some embodiments, open-ended tube 520c may be made of a fire-polished glass, so that tube distal end 513c does not include any sharp edges. That is, inner rim 527c and an outer rim 529c of flange 525c are rounded and may be pressed against the skin of a subject without risk of cutting or puncturing the skin. According to some embodiments, flange 525c may be shaped and dimensioned such as to ensure that when pressed against the skin of a subject, tube distal end 513c fluidly-seals open-ended tube 520c. Alternatively, or additionally, flange 525c may have positioned thereon a smooth, and optionally elastic, cover or coating (not shown), such as a rubber or rubber-like cover or coating. The cover or coating may be configured to both protect the skin from cuts and fluidly-seal tube distal end 513c when flange 525c is pressed against the skin.

Also indicated in FIG. 5C are a cap cathode 505c, an electrical connection member 509c, a hollow needle member 515c, and an applicator gas port 519c, which may be essentially similar to cap cathode 505b, electrical connection member 509b, needle member 515b, and applicator gas port 519b, respectively, of applicator 508b.

Needle member 515c may extend in the distal direction into open-ended tube 520c from applicator gas port 519c. Applicator 508c is thus configured to allow controlling air-pressure within open-ended tube 520c when pressed against the skin of a subject. In particular, applicator 508c is configured to allow reducing the air-pressure within open-ended tube 520c to sub-atmospheric pressures at the start of a treatment (after pressing flange 525c against the skin of a subject), or mixing the air with an inert gas (such as neon or argon) or even substantially replacing the air with an inert agas. According to some such embodiments, applicator 508c may constitute a specific embodiment of applicator 308, applicator 308', or applicator 408, being thereby configured to be mounted on handle 306, handle 306', or handle 406, respectively.

Referring to FIG. 5D, depicted is an applicator 508d, according to some embodiments. According to some embodiments, applicator 508d may be configured for desiccation (and, optionally, cauterizing and/or ablation) treatments. Applicator 508d differs from applicator 508a in further including a collimator 535d made of an electrically conducting material (e.g. a metal) and mounted on the distal portion of a closed tube 520d of applicator 508a. Apart from the addition of collimator 535d, applicator 508d may be essentially similar to applicator 508a. Collimator 535d is mounted externally to closed tube 520d. Collimator 535d may be shaped similarly to a funnel, including a collimator proximal portion 537d which tapers in the distal direction, and a collimator distal portion 539d, which may be shaped as a narrow tube.

Also indicated in FIG. 5D is a collimator tip 541d. Collimator tip 541d shape may be characterized by sharp angles, such as to facilitate the formation of corona discharges or sparks. As a non-limiting example, and as depicted in FIG. 5D, collimator tip 541 may be square-shaped.

Collimator 535d is configured to focus an applied plasma discharge. More specifically, according to some embodiments, in operation, an electric field, induced by the plasma discharge inside closed tube 520d, polarizes collimator 535d, leading to a corona discharge or spark from collimator tip 541d. Applicator 508d may thus be used when treating smaller skin growths/abnormalities and/or when greater intensity is required.

Also indicated in FIG. 5D are a cap cathode 505d and an electrical connection member 509d, which may be essentially similar to cap cathode 505a and electrical connection member 509a of applicator 508a.

According to some embodiments, not depicted in the figures, there is provided an applicator for a cold-plasma discharge device. The applicator differs from applicator 508d in that the (cap) cathode thereof includes a hollow needle member (i.e. a hollow needle) but may otherwise be essentially similar to applicator 508d. The needle member may be essentially similar to needle member 515b of applicator 508b. According to some embodiments, the applicator may be configured for desiccation (and, optionally, cauterizing and/or ablation) treatments.

Figure 5E:
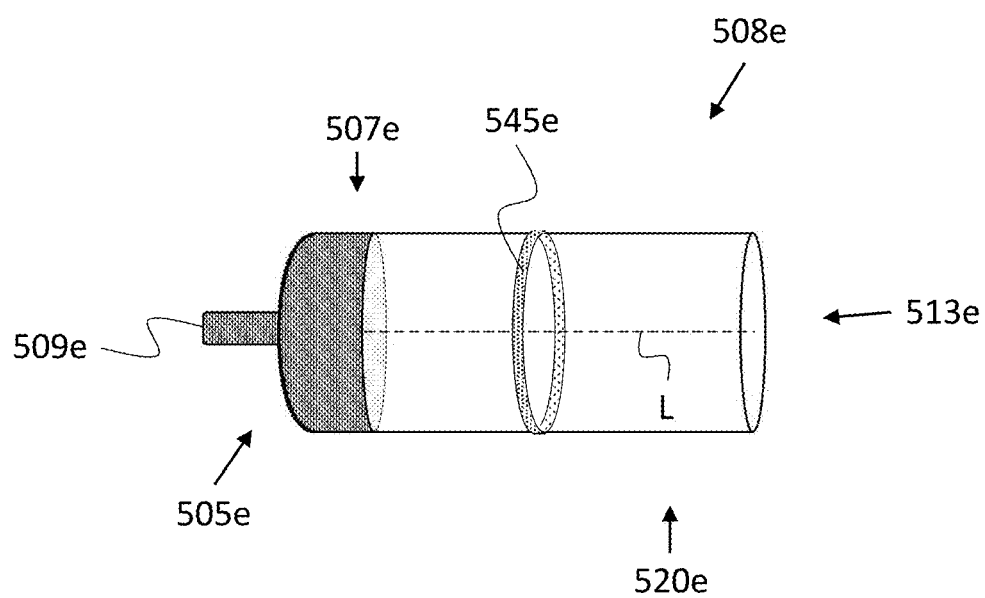

Referring to FIG. 5E, depicted is an applicator 508e, according to some embodiments. According to some embodiments, applicator 508e may be configured for skin rejuvenation, drying, and ozone therapy. Applicator 508e differs from applicator 508a in including a plasma control ring 545e but may otherwise be essentially similar thereto. Plasma control ring 545e may be disposed about a closed tube 520e (externally thereto) and distally to a proximal portion 507e of closed tube 520e. Plasma control ring 545e is electrically conducting. Electrical wires coupling plasma control ring 545e to a flyback amplifier in a handle, whereon applicator is to be mounted, are not shown.

Plasma control ring 545e is configured to generate an oscillating magnetic field within closed tube 520e. The oscillating magnetic field may be substantially parallel to a longitudinal axis L (i.e. a central axis) of applicator 508e, alternating between substantially pointing in the distal direction and substantially pointing in the proximal direction. Plasma control ring 545e is thus configured to collimate a plasma discharge generated within closed tube 520e.

Also indicated in FIG. 5E are a cap cathode 505e, an electrical connection member 509e, and a tube distal end 513e, which may be essentially similar to cap cathode 505a, electrical connection member 509a, and tube distal end 513a, respectively, of applicator 508a.

According to some embodiments, not depicted in the figures, there is provided an applicator for a cold-plasma discharge device. The applicator differs from applicator 508b in including a plasma control ring but may otherwise be essentially similar to applicator 508b. The plasma control ring may be essentially similar to plasma control ring 545e of applicator 508e. According to some embodiments, the applicator may be configured for skin rejuvenation, drying, and ozone therapy.

According to some embodiments, not depicted in the figures, there is provided an applicator for a cold-plasma discharge device. The applicator differs from applicator 508c in including a plasma control ring but may otherwise be essentially similar to applicator 508c. The plasma control ring may be essentially similar to plasma control ring 545e of applicator 508e. According to some embodiments, the applicator may be configured for desiccation (and, optionally, ablation) treatments of warts.

According to some embodiments, not depicted in the figures, there is provided an applicator for a cold-plasma discharge device. The applicator differs from applicator 508d in including a plasma control ring but may otherwise be essentially similar to applicator 508d. The plasma control ring may be essentially similar to plasma control ring 545e of applicator 508e.

According to some embodiments, not depicted in the figures, there is provided an applicator for a cold-plasma discharge device. The applicator differs from applicator 508*d* in including a needle member and a plasma control ring but may otherwise be essentially similar thereto. The needle member may be essentially similar to needle member 515*b* of applicator 508*b*. The plasma control ring may be essentially similar to plasma control ring 545*e* of applicator 508*e*.

As used herein, according to some embodiments, the term "tube" is used in a broad sense to cover not only tube having a circular cross-section, but also tubes otherwise shaped cross-sections, such as elliptical cross-sections, triangular cross-sections, rectangular cross-sections, and more generally, any simple polygonal cross-section, including concave polygonal cross-sections. Further it is to be understood the term "tube" is not limited to shapes having a fixed cross-section. For example, as used herein, the term "tube" also covers conical tubes or tubes whose radius tapers off towards each of the two ends of the tube.

As used herein, according to some embodiments, the terms "ground terminal" and "anode" may be used interchangeably.

As used herein, according to some embodiments, the terms "capsule" and "tube" may be used interchangeably.

Methods

Figure 6:
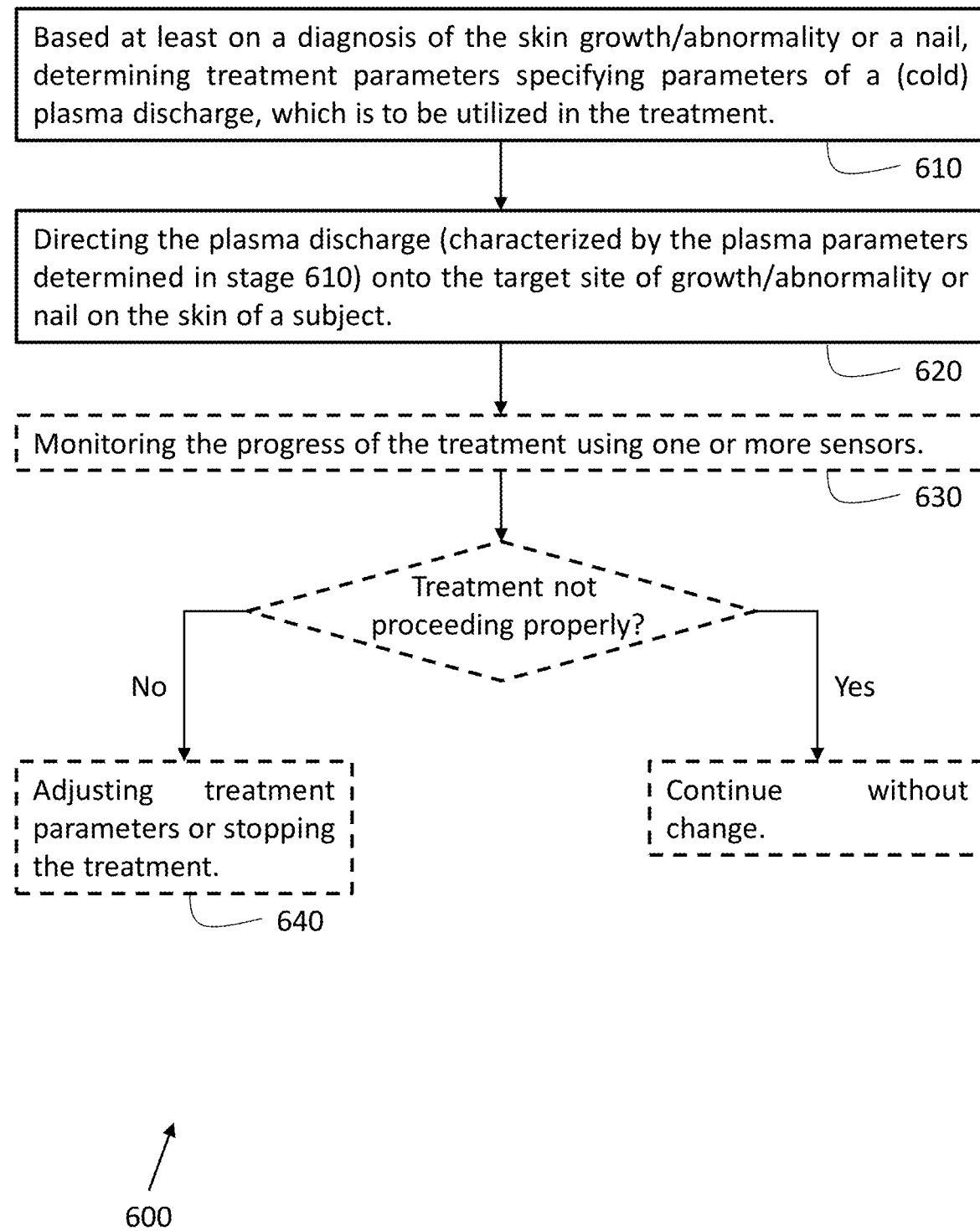
FIG. 6 is a flowchart of a method for treating skin tissue using cold plasma, according to some embodiments.

According to an aspect of some embodiments, there is provided a method for treating non-malignant skin growths and abnormalities using (cold) plasma. FIG. 6 presents a flowchart of such a method, a method 600, according to some embodiments. Method 600 may be implemented using system 200 and systems similar thereto. In particular, method 600 may be implemented using any one of system 100, system 300 (and specific embodiments thereof which include discharge device 302'), and system 400, and systems similar thereto, which may include applicators such as applicators 508*a*, 508*b*, 508*c*, 508*d*, and 508*e*, the rest of the applicators described above, and applicators similar thereof.

Before going into the specifics of method 600, a brief overview of the method is provided. In applying method 600, the electrons, in a generated cold plasma discharge, are directed onto a treatment site on the subject, such as to close an electrical conduction path through the treatment site. The treatment site may include a skin growth or abnormality intended for removal or a nail disease or disorder. The cold plasma discharge may be produced by a self-sustaining Townsend avalanche, or even a subnormal glow discharge, such that the electric current through the treatment site does not, or substantially not, heat the treatment site and tissue around the target site. The plasma discharge may be composed of a series of discharge pulses or may otherwise continuously vary in time. The resulting electrical current may have an average amplitude between about 0.1 mA and 10 mA and may be further characterized by an average power between about 0.1 µW and about 10 µW.

Without committing to any physical theory or biological mechanism, according to some embodiments, the observed therapeutic effects (as shown, for example, in FIGS. 10A-12B) may be attributed to the electromagnetic interaction of the applied cold plasma discharge with tissue at the treatment site. More specifically, according to some embodiments, the application of a time-varying cold plasma discharge, as described above and in more detail below, onto a treatment site including a skin growth/abnormality or a nail disease/disorder may trigger cellular and extra-cellular signaling processes, and thereby initiate biological processes such as enzyme reactions, membrane transport, and cell proliferation and differentiation. According to some embodiments, the application of a time-varying cold plasma discharge, as described above and in more detail below, onto a target tissue including a skin growth/abnormality may induce the formation time-varying magnetic fields at the target site. These time-varying magnetic fields may induce (electrical) eddy currents in the target tissue, which in turn may initiate the biological processes described above.

According to some embodiments, method 600 includes:

A set up stage 610, wherein treatment parameters are determined based at least on a diagnosis of the skin growth/abnormality. The treatment parameters include the plasma parameters specifying the properties of the (cold) plasma discharge—which is to be utilized in the treatment—such as the average power of the plasma discharge, the amplitude of the plasma current, the width(s) of the voltage pulses, the pulse frequency (i.e. the frequency of the carrier wave within a pulse), the inter-pulse(s) separation, the shape(s) of the voltage pulses, and so on.

A treatment stage 620, wherein a (cold) plasma discharge, characterized, or substantially characterized, by the plasma parameters determined at set up stage 610, is generated—using a discharge system, such as discharge system 200, 100, 300, or 400—and directed onto the target site on the skin of a subject.

It is noted that the use of pulses may be especially relevant for treating lesions and other skin and nail diseases and disorders. The carrier wave of the pulse may be configured to facilitate deep penetration into the lesion or the disordered/diseased skin or nail, while the signal riding on the carrier wave (i.e. the envelope) may be configured to treat the lesion or the skin/nail disease or disorder.

The terms "skin diseases/disorders" and "nail diseases/disorders", as used herein, may be interchangeable, in some embodiments. In this context, "skin" and "nail" may be interchangeable in some embodiments.

The terms "lesion" and "skin growths/abnormalities", as used herein, are interchangeable and generally refer to skin abnormalities, including, but not limited to, non-malignant skin growths, topical external disorders, skin lesions, skin tags, pigmentation, moles, viral warts, acne, ulcers, and wounds.

The terms "nail diseases" and "nail disorders" as used herein, include, but are not limited to, nail fungus infections.

The treatment parameters may further specify preparation parameters, such as the pressure of the gas that is to be ionized and the composition thereof, as well as the type of applicator to be utilized, and the distance from the target site that the distal tip of the applicator must be positioned in order to generate the plasma discharge. In this last regard, it is noted that the closing of a conduction path (including the target tissue) through the air about the target site may lead the formation of ozone at the target site. As a further advantage, being a powerful oxidant, the ozone may act as a disinfectant at the target site.

The treatment parameters may further include the prescribed duration of the application of the plasma discharge (onto the target site), or, if more than one treatment is anticipated/prescribed, the duration of at least the first treatment. Alternatively, according to some embodiments, the treatment parameters may specify that the plasma discharge is to continue being applied until the plasma discharge self-terminates. Without committing to any physical theory or biological mechanism, according to some embodiments, the self-termination of the plasma discharge may be brought about by alterations to the target tissue due to the activation of cellular and extra-cellular signaling processes as described above. According to some such embodiments, the self-termination of the plasma discharge may indicate that the plasma discharge has been applied for a sufficient duration.

It is noted that application of a resonant frequency electrical current to a tissue may lead to polarization of the tissue and a consequent increase in the electrical conductivity of the tissue. According to some embodiments, the frequencies and shapes of the voltage pulses inducing the cold plasma discharge may thus be chosen to selectively increase the electrical conductivity of a skin growth/abnormality, while substantially leaving the electrical conductivity of surrounding normal tissue unaffected.

Figure 8A:
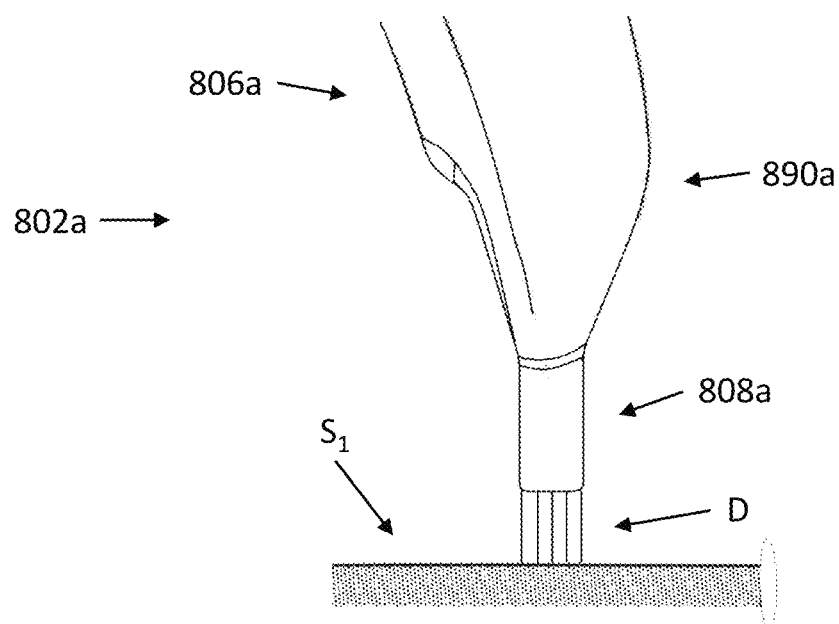
FIGS. 8A-8D schematically depict use of three different cold-plasma discharge devices for treating skin tissue using cold plasma, according to some embodiments.
Figure 8B:
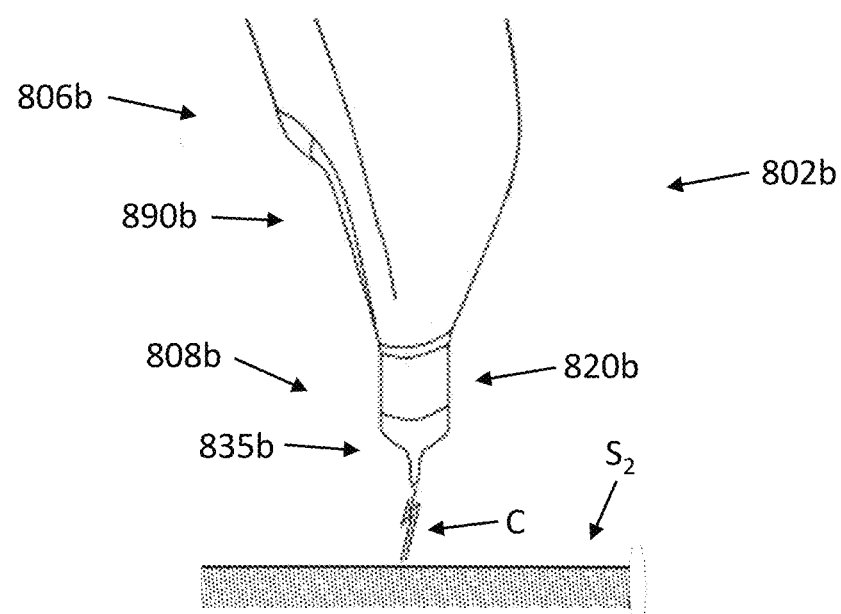
Figure 8C:
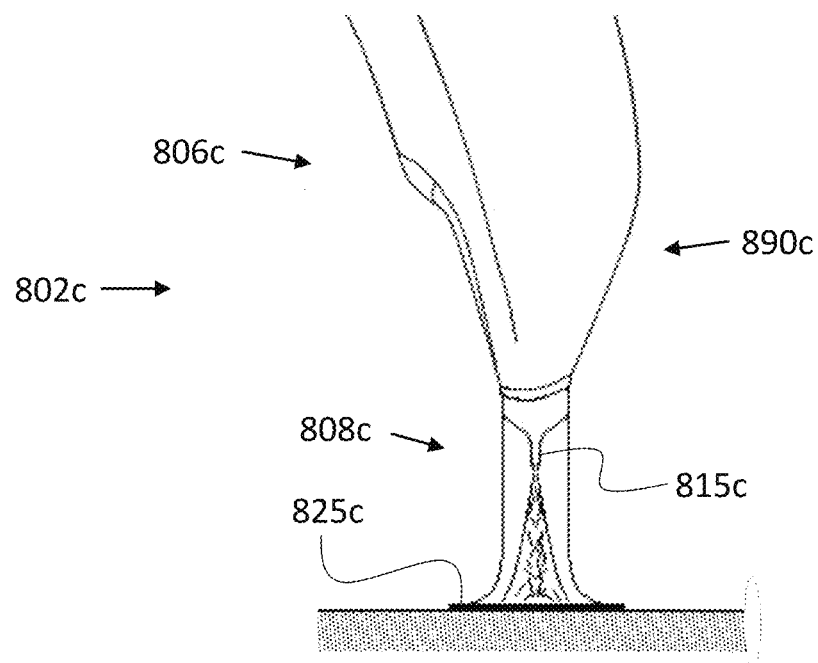

At the beginning of treatment stage 620, an applicator of the discharge device employed, may be brought near the target site (e.g. when the applicator includes a closed tube, as is the case with applicators 508*a*, 508*b*, 508*d*, and 508*e*, which thus constitute dielectric barrier discharge (DBD) devices (at least in the sense of including inside the closed bulb a dielectric medium, such as inert gas, air, or a mixture thereof, at sub-atmospheric pressure), or pressed against the skin of the subject around the target site (e.g. when the applicator includes an open-ended tube, as is the case with applicator 508*c*), such that when a sufficiently high voltage is produced at the applicator electrode, an electrical circuit including the target site is closed and a plasma discharge is generated. More specifically, the cathode (i.e. the electrode in the applicator) is positioned sufficiently close to the target site (essentially as depicted in FIGS. 8A-8C), such as to allow closing a conduction path via the target site (e.g. by increasing the voltage beyond a threshold voltage). According to some embodiments, to allow closing the conduction path, the cathode-target site distance may be set to between about 1 mm and about 5 mm. More generally, the electrode-target site distance may depend on the frequency of the voltage pulses.

According to some embodiments, the cathode may first be positioned near the target site. The voltage is then increased until the electrical circuit through the target site is closed. The voltage may then be slowly further increased until the average power reaches a desired value. Alternatively (or additionally), the distance between the cathode may be brought slowly brought closer to the target site until the desired value of the average power is achieved (the average power of the plasma discharge being dependent on the cathode-target site distance). Further fine tuning may be effected by adjusting the duty cycle.

Figure 7:
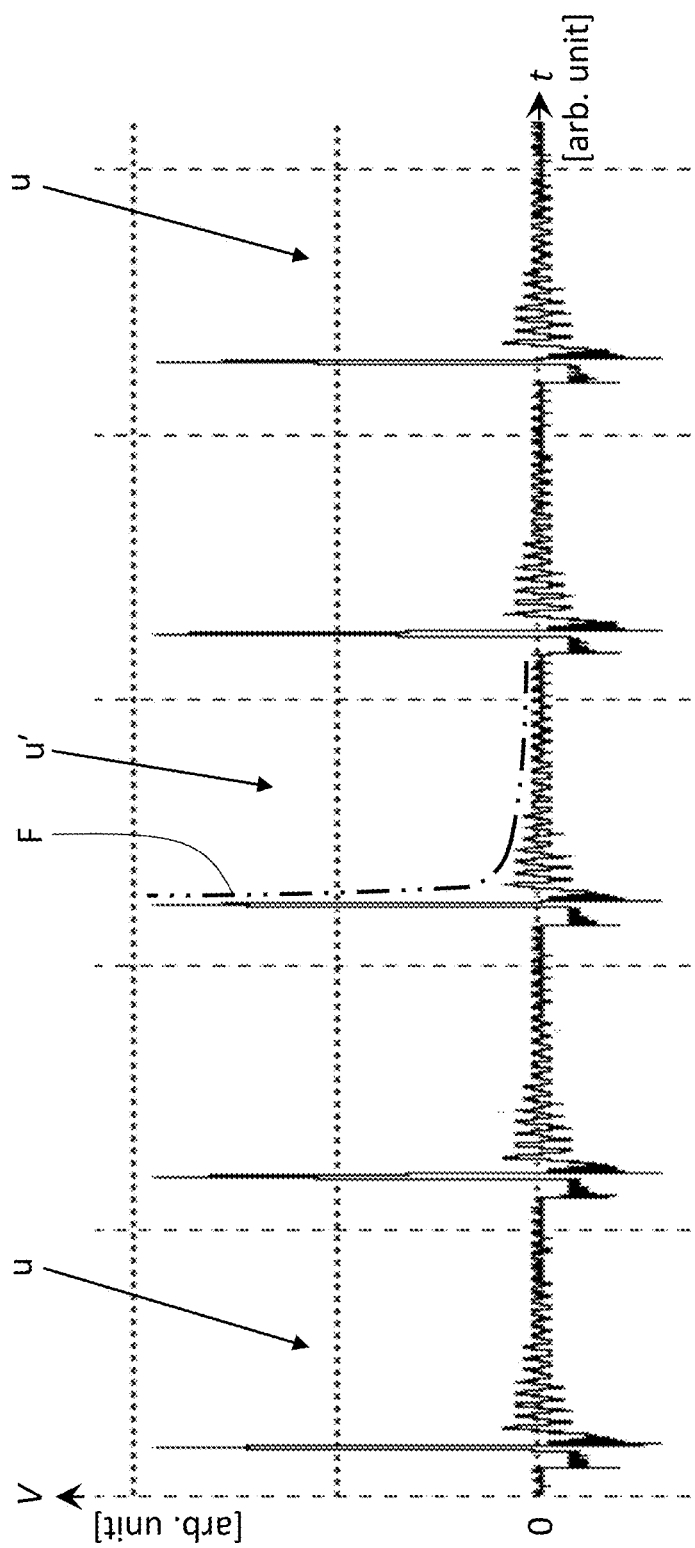
FIG. 7 schematically depicts a series of voltage pulses used to induce a respective series of cold plasma discharge pulses, such as to close an electrical circuit through a target site on the skin of a subject, according to the method of FIG. 6 and using the system of FIG. 2, according to some embodiments.

Referring also to FIG. 7, FIG. 7 is a graph of voltage as a function of time. The values of the voltage are given in terms of arbitrary units. Similarly, the time is measured in arbitrary units. FIG. 7 provides an example of voltage generated at the cathode (e.g. the cathode of applicator 208) in treating certain types of skin conditions according to method 600 and using system 200, according to some embodiments thereof. More specifically, a series of voltage pulses u is depicted. Each of the pulses is modulated by a sharply decaying envelope. An envelope of one of the voltage pulses, a voltage pulse u', is explicitly indicated by dashed-double-dotted curve F.

According to some embodiments, the rise time of the voltage pulse—that is, the time (from the beginning of the voltage signal) until the peak voltage is attained—may be extremely rapid, for example, about 2 nsec, necessitating the use of high-frequency components ~0.5 GHz. The frequency at which the pulses are repeated may be between about 50 kHz and about 50 MHz. That is, at least about an order of magnitude slower than the higher-frequency components. By "playing" with the peak voltage and the duty cycle (i.e. the rate at which the pulses are repeated), the duty cycle and the high voltage, the amount of energy "deposited" in a lesion may be controlled.

Optionally, method 600 may include a monitoring stage 630 implemented during treatment stage 620, wherein the treatment may be monitored by one or more sensors. The sensor data may be analyzed (in real-time) to ensure that the treatment is proceeding properly ("smoothly"). More specifically, sensor data may be analyzed to ensure that the values of the plasma parameters are in fact the desired values (i.e. the parameter values determined in set up stage 610), or substantially the desired values, and that the subject is reacting well to the treatment. In particular, camera images of the plasma may be used to determine whether the plasma is in fact at skin temperature.

Optionally, method 600 may further include a treatment adjustment stage 640—contingent on it being determined in monitoring stage 630 that the treatment is not proceeding properly—wherein treatment parameters may be adjusted in real-time (i.e. during treatment stage 620) or the treatment may be terminated early or even aborted (e.g. in the event of a malfunction). In particular, plasma parameters may be adjusted to the initially desired values (determined in set up stage 610) or changed from the initially desired values to new values, based on the monitoring data. According to some embodiments, based on the monitoring data, the treatment may be prolonged or terminated early.

According to some embodiments, in set up stage 610, the treatment parameters may be determined additionally taking into account personal data of the subject, such as age, gender, weight, and medical history. When the subject has already gone a treatment(s) using method 600, whether to the same skin growth/abnormality or a different skin growth/abnormality, the medical history may include the reaction of the subject to the past treatment(s), e.g. success of the treatment, healing rate, and so on. The determination of the treatment parameters may be performed using a computerized system such as computerized advisory center 280.

FIGS. 8A-8C schematically depict application of a cold-plasma discharge to a target site utilizing three different applicators, respectively, according to some embodiments. Referring to FIG. 8A, depicted are a distal section 890*a* of a handle 806*a* and an applicator 808*a* of a cold-plasma discharge device 802*a*, according to some embodiments. As a non-limiting example, discharge device 802*a* may be a specific embodiment of any one of discharge devices 102, 302, 302', and 402, wherein each of applicators 108, 308, 308', and 408, respectively, is a specific embodiment of one of applicators 508*a*, 508*b*, and 508*e*. A plasma discharge D, applied by discharge device 802*a* onto a target site on a skin surface $S_1$ of a subject, is depicted.

Referring to FIG. 8B, depicted are a distal section 890*b* of a handle 806*b* and an applicator 808*b* of a cold-plasma discharge device 802*b*, according to some embodiments. As a non-limiting example, discharge device 802*b* may be, for example, a specific embodiment of any one of discharge devices 102, 302, 302', and 402, wherein each of applicators 108, 308, 308', and 408, respectively, is a specific embodiment of applicator 508*d*. A (closed) tube 820*b* of applicator 808*b* has mounted thereon a metallic collimator 835*b*, which may be a specific embodiment of metallic collimator 535*b*, and which may be used to generate a corona discharge C or a spark applied onto a target site on a skin surface $S_2$ of a subject. As compared to discharged device 802*a*, discharge device 802*b* may be used for treating comparatively smaller skin growths/abnormalities or skin growths/abnormalities requiring comparatively higher intensity of the plasma discharge.

Referring to FIG. 8C, depicted are a distal section 890c of a handle 806c and an applicator 808c of a cold-plasma discharge device 802c, according to some embodiments. As a non-limiting example, discharge device 802c may be, for example, a specific embodiment of any one of discharge devices 302, 302', and 402, wherein each of applicators 308, 308', and 408, respectively, is a specific embodiment of applicator 508c.

Also indicated in FIG. 8C are a needle member 815c and a flange 825c of applicator 808c, which may be specific embodiments respectively of needle member 515c and flange 525c of applicator 508c.

It is noted that in FIGS. 8A and 8B the ambient air about the target site is indirectly ionized by the cathode in the applicator. That is, a DBD is employed. In contrast, in FIG. 8C the air about the target site is directly ionized by the cathode in the applicator.

Figure 8D:
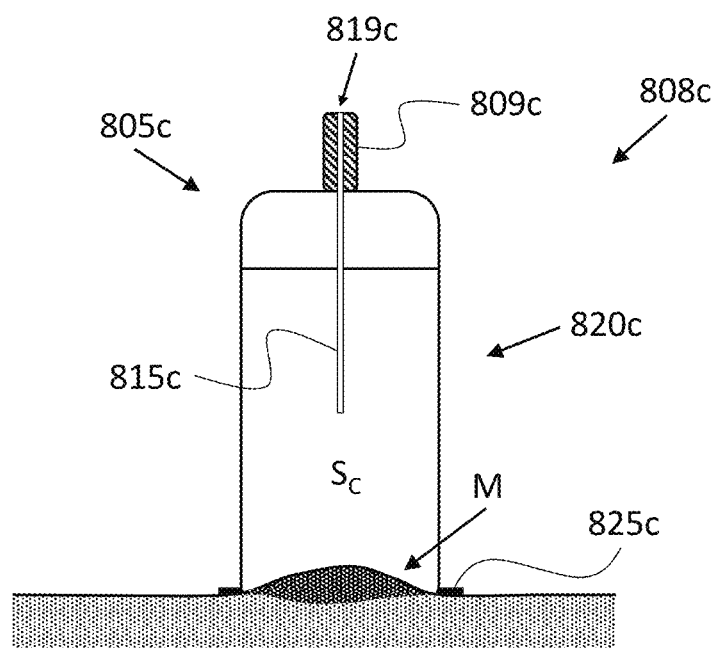

FIG. 8D is a schematic cross-sectional view of applicator 808c, according to some embodiments. Applicator 808c is depicted placed on a target site on the skin of a subject with suction applied (through needle member 815c), thereby pulling a lesion M in the target site into an open-ended tube 820c of applicator 820c. Advantageously, pulling lesion M into open-ended tube 820c may assist the treatment by facilitating the focusing of the plasma discharge on lesion M.

Also indicated in FIG. 8D are a cap cathode 805c, an electrical connection member 809c, and an applicator gas port 819c of applicator 808c, which may be specific embodiments respectively of cap cathode 505c, electrical connection member 509c, and applicator gas port 519c of applicator 508c.

Figure 9A:
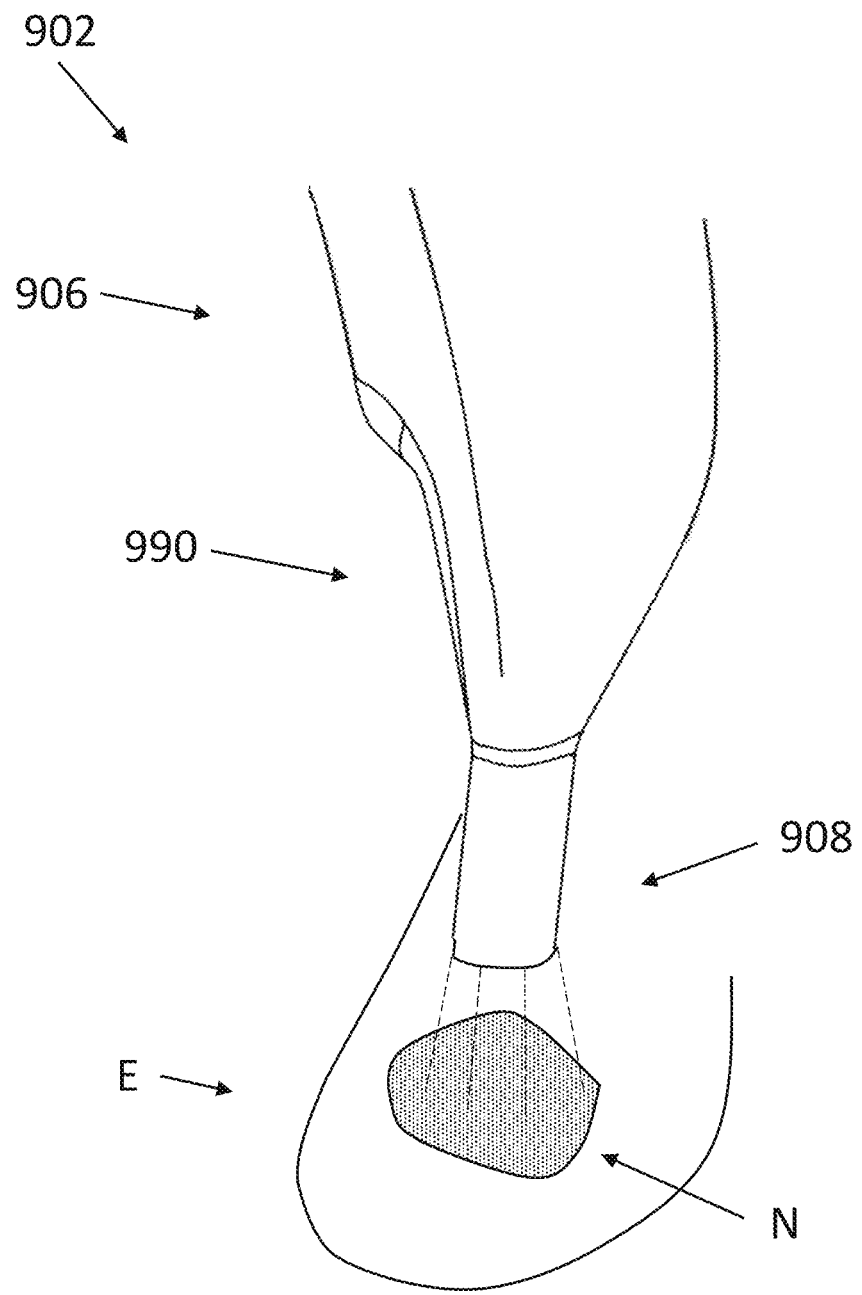
FIG. 9A schematically depicts use of a cold-plasma discharge device for treating nail fungus, according to some embodiments.

FIG. 9A schematically depicts treatment of nail fungus with cold plasma using a cold-plasma discharge device 902, according to some embodiments. Depicted are a distal section 990 of a handle 906 and an applicator 908 of discharge device 902, according to some embodiments. Also depicted is a big toe E and a toenail N of a subject. In this exemplary embodiment, the toenail N has a fungal infection. As a non-limiting example, discharge device 902 may be a specific embodiment of any one of discharge devices 102, 302, 302', and 402, wherein each of applicators 108, 308, 308', and 408, respectively, is a specific embodiment of one of applicators 508a, 508b, and 508e.

Figure 9B:
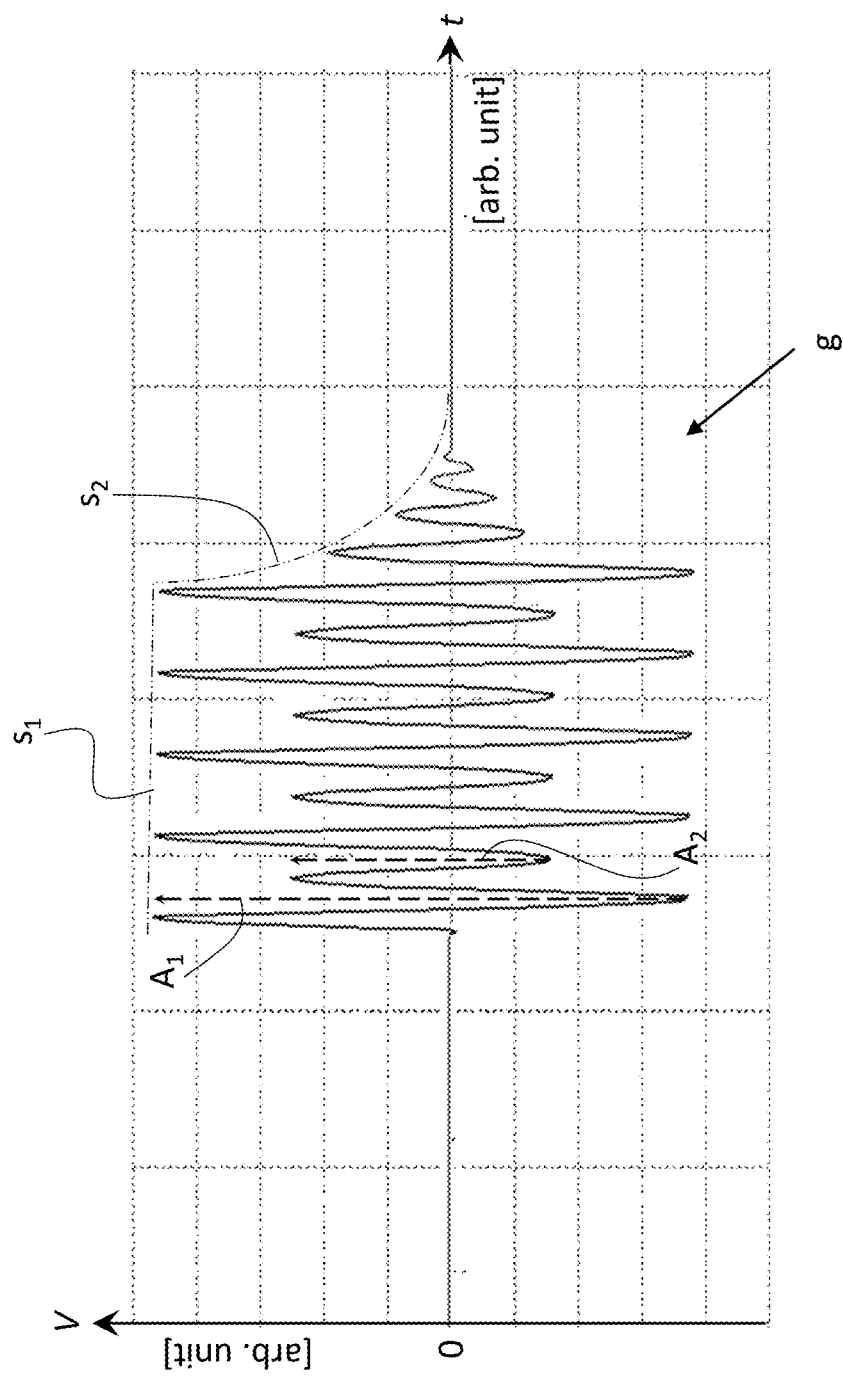
FIG. 9B schematically depicts the waveform of a double-modulated voltage pulse utilized by the discharge device of FIG. 9A in treating the nail fungus, according to some embodiments.

Referring also to FIG. 9B, FIG. 9B is a graph of voltage as a function of time. The values of the voltage are given in terms of arbitrary units. Similarly, the time is measured in arbitrary units. FIG. 9B provides an example of a voltage pulse, which may be generated at the cathode of applicator 908 during the course of treating the fungal infection at the toenail N, according to some embodiments. More specifically, a voltage pulse g is depicted. The voltage pulse g includes two differently modulated segments: a first segment $s_1$ and a second (and later) segment $s_2$. In the segment $s_1$, the envelope of the carrier wave is flat or slowly decaying. In the segment $s_2$, the envelope of the carrier wave decays exponentially or substantially exponentially. The carrier wave is further modulated, as indicated by the presence of two sets of alternating amplitudes $A_1$ and $A_2$ (each indicated by a respective dashed double-headed arrow). In other words, the carrier wave is doubly-modulated. According to some embodiments, the envelope may facilitate penetrating the toenail, while the carrier wave may treat the fungus at the depth of penetration.

EXAMPLES

This subsection presents results of topical treatments, which demonstrate the efficacy of the disclosed systems and methods. Without being bound by any theory or mechanism of action, one possible explanation for observed treatments results (shown below) is that the applied cold plasma discharge pulses deactivate the capillaries within a skin lesion/abnormality, thereby inhibiting blood supply thereto. As a result, the skin lesion decays and shrinks (so as to ultimately vanish) and/or falls off. In contrast, blood supply in the healthy tissue surrounding the skin lesion remains unaffected/normal, and may even improve (namely, increase), possibly as a result of the shrinking/disappearing of the skin lesion and the alleviated burden on blood circulation associated with the skin lesion. Thus, treatment of the skin lesion, and the corresponding normal or improved blood circulation, may induce skin rejuvenation. This differential activity may potentially additionally be due to variances between the electrical conductivity of healthy tissue and skin lesions/abnormalities. These variances may result from differences in the structure of healthy tissue and skin lesions/abnormalities. The blood vessels in healthy tissue are well formed, leading to proper supply of blood to the tissue. In contrast, the blood vessels in skin lesions/abnormalities may typically be deformed, leading to inadequate supply of blood. Additionally, or alternatively, it is suggested that the observed treatment results may be at least partially attributed to ozone produced during the treatment. The production of ozone oxidizes the skin lesion/abnormality, leading to deactivation of the capillaries therein, essentially as described above.

Example 1—Pigmentation Removal/Bleaching Treatment with Cold Plasma

Figure 10C:
FIGS. 10A-10C present results of pigmentation removal treatment using the devices and methods of the present disclosure.
Figure 10B:
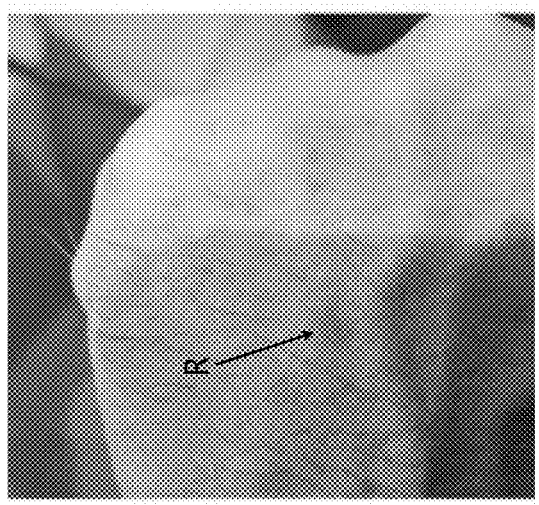
Figure 10A:
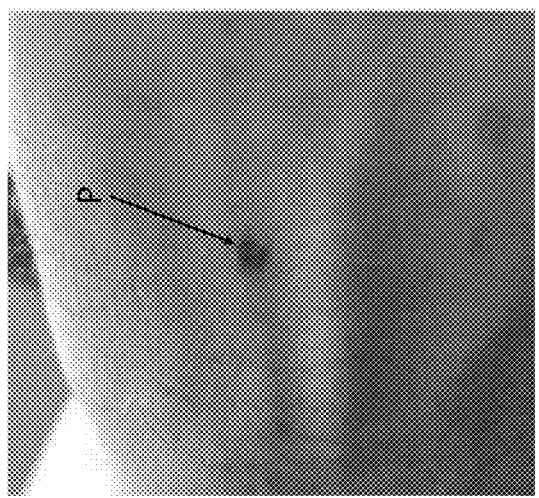

Referring to FIGS. 10A-10C, the results of a pigmentation removal/bleaching treatment—using the devices and methods of the present disclosure—are presented. More specifically, a pigmented spot P, on the back of a hand (i.e. the dorsal side of the hand) of a subject, was treated. Three greyscale photos of the back of the hand are presented during different stages of the treatment. FIGS. 10A, 10B, and 10C depict the pigmented spot P a day after the treatment (day 1), eleven days after the treatment (day 11), and twenty-three days after the treatment (day 23), respectively. At day 1 (FIG. 10A), the pigmented spot P is clearly visible. At day 11 (FIG. 10B), the pigmented spot is no longer visible. Instead, a slightly reddened spot R (indistinguishable in FIG. 10B from slight pigmentation since the photo is greyscale) is apparent at the location wherein the pigmented spot P was formerly present/visible. At day 23 (FIG. 10C), the pigmented spot P is no longer visible, and the reddened spot R vanished.

Example 2—Skin Tag Removal with Cold Plasma

Figure 11C:
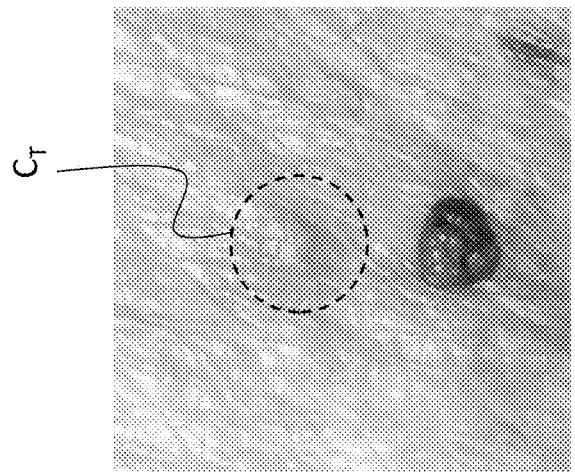
FIGS. 11A-11C present results of a skin tag removal treatment using the devices and methods of the present disclosure.
Figure 11B:
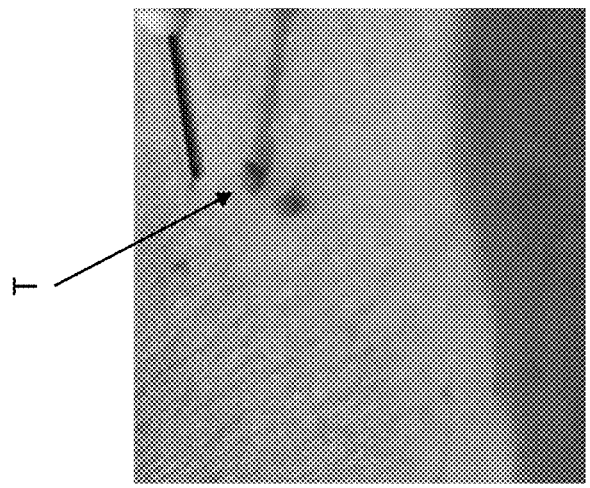
Figure 11A:
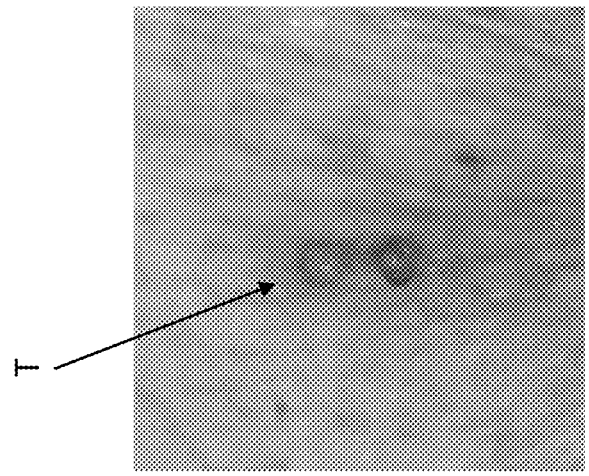

Referring to FIGS. 11A-11C, the results of a skin tag removal treatment—using the devices and methods of the present disclosure—are presented. More specifically, a skin tag T on the skin of a subject was treated. FIGS. 11A, 11B, and 11C depict the skin tag T before, during, and about ten days after the treatment, respectively. As can be seen, already during treatment, the treated skin tag has shrunk (FIG. 11B). About ten days after treatment the skin tag T has substantially disappeared, as can be seen by examining the area encircled by a circle CT, which surrounds the region where skin tag was located prior to treatment (FIG. 11C).

Example 3—Viral Wart Removal with Cold Plasma

Figure 12B:
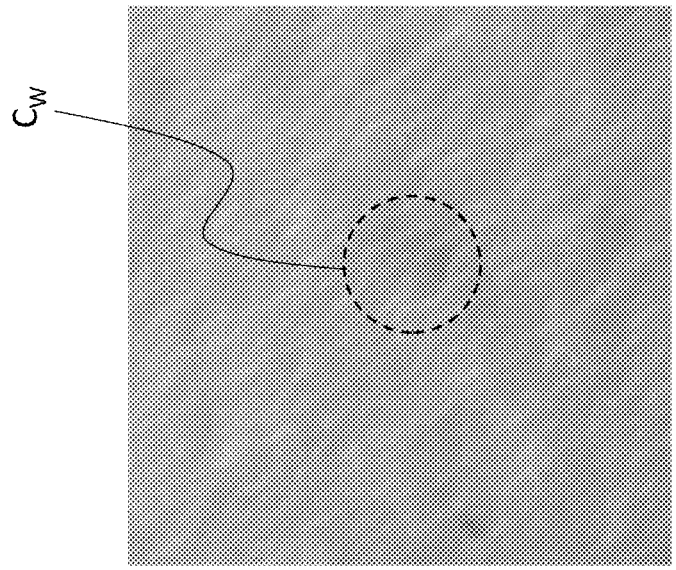
FIGS. 12A and 12B present results of a viral wart removal treatment using the devices and methods of the present disclosure.
Figure 12A:
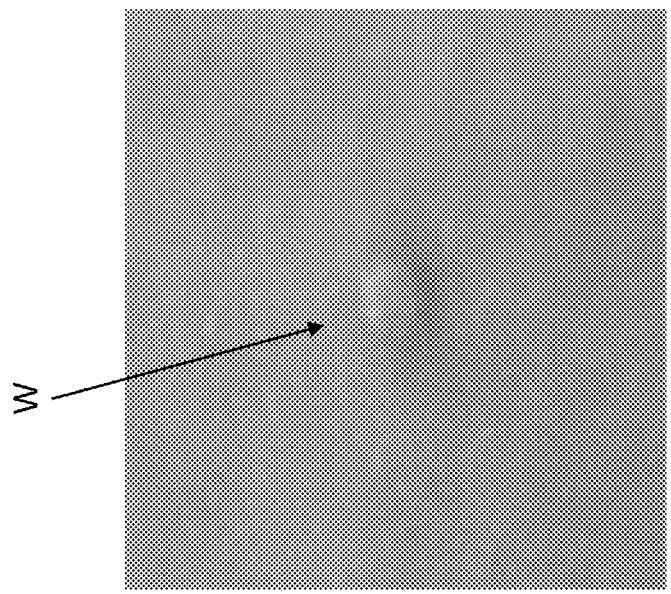

Referring to FIGS. 12A and 12B, the results of a viral wart removal treatment—using the devices and methods of the present disclosure—are presented. More specifically, a viral wart W on the skin of a subject was treated. FIGS. 12A and 12B are photos of the treated area before treatment and about fourteen days after treatment, respectively. Post-treatment, the viral wart W is no longer visible (FIG. 12B). A circle $C_W$ surrounds the region where the viral wart W was formerly present.

It is appreciated that certain features of the disclosure, which are, for clarity, described in the context of separate embodiments, may also be provided in combination in a single embodiment. Conversely, various features of the disclosure, which are, for brevity, described in the context of a single embodiment, may also be provided separately or in any suitable sub-combination or as suitable in any other described embodiment of the disclosure. No feature described in the context of an embodiment is to be considered an essential feature of that embodiment, unless explicitly specified as such.

Although stages of methods according to some embodiments may be described in a specific sequence, methods of the disclosure may include some or all of the described stages carried out in a different order. A method of the disclosure may include a few of the stages described or all of the stages described. No particular stage in a disclosed method is to be considered an essential stage of that method, unless explicitly specified as such.

Although the disclosure is described in conjunction with specific embodiments thereof, it is evident that numerous alternatives, modifications, and variations that are apparent to those skilled in the art may exist. Accordingly, the disclosure embraces all such alternatives, modifications and variations that fall within the scope of the appended claims. It is to be understood that the disclosure is not necessarily limited in its application to the details of construction and the arrangement of the components and/or methods set forth herein. Other embodiments may be practiced, and an embodiment may be carried out in various ways.

The phraseology and terminology employed herein are for descriptive purpose and should not be regarded as limiting. Citation or identification of any reference in this application shall not be construed as an admission that such reference is available as prior art to the disclosure. Section headings are used herein to ease understanding of the specification and should not be construed as necessarily limiting.

What is claimed is:

1. A system for treating skin and nails with cold plasma, the system comprising a discharge device, which comprises a handle and an applicator, and control infrastructure, which comprises a waveform generator;
    wherein the applicator comprises an elongated tube, extending from a tube proximal end to a tube distal end, and a cathode housed within the tube, the tube being mounted, via the tube proximal end, on a distal tip portion of the handle;
    wherein the handle comprises a flyback amplifier functionally associated with the waveform generator and electrically associated with the cathode, the waveform generator being configured to induce the flyback amplifier to apply a voltage at the cathode;
    wherein the voltage produced by the flyback amplifier is configured to allow generating a self-sustaining Townsend avalanche when the tube distal end is positioned sufficiently near a target site on a skin surface or a nail of a subject, such as to produce a cold plasma discharge directed at the target site, the cold plasma discharge having an average electrical current amplitude in the range of about 0.1 mA to about 10 mA and an average power in the range of about 0.1 µW to about 10 µW, the system being thereby configured to treat the target site without heating thereof; and
    wherein the tube distal end is open and configured to be pressed against skin of a subject around a target site, such as to fluidly seal the tube distal end, wherein the control infrastructure further comprises a vacuum pump fluidly coupled to the tube via an applicator gas port on the tube proximal end, such as to allow withdrawing gas from the tube, and wherein, optionally, the cathode comprises a needle extending longitudinally within the tube.

2. The system of claim 1, wherein the waveform generator and the flyback amplifier are electrically coupled, and wherein the flyback amplifier is configured to amplify a voltage signal produced by the waveform generator, such that an instantaneous magnitude of the voltage applied at the cathode is dependent on the instantaneous magnitude of the voltage signal.

3. The system of claim 1, wherein the voltage applied at the cathode is characterized by a series of pulses having a duty cycle in the range of 1% to 70%, wherein each pulse has a pulse width in the range of about 10 nsec to about 200 nsec, and wherein a frequency spectrum of the pulse includes one or more frequencies in the range of about 10 kHz to about 1 GHz.

4. The system of claim 3, wherein one or more of the pulses in the series of pulses are amplitude modulated, double-modulated, or harmonically modulated, and/or wherein one or more of the pulses in the series of pulses are amplitude modulated by a monotonically decreasing function.

5. The system of claim 1, wherein the tube is closed on the tube distal end and comprises an inert gas and/or air at a sub-atmospheric pressure of at least about 2 kPa or higher.

6. The system of claim 5, wherein dimensions and shape of the tube distal end are adapted to a group of lesions or a group of nails having common dimensions, shape, and/or texture.

7. The system of claim 5, wherein the applicator is detachably mounted on the handle.

8. The system of claim 1, wherein the cathode comprises a transversely extending surface, which extends over at least about 25% of a transverse cross-section of the tube, the applicator being thereby configured for dielectric-barrier discharge; or
    wherein the cathode comprises a needle extending longitudinally within the tube, and/or wherein the applicator further comprises an electrically-conducting collimator, which is mounted on the tube distal end, the discharge device being thereby configured for corona discharge or spark discharge.

9. The system of claim 1, wherein the control infrastructure further comprises a vacuum pump fluidly coupled to the tube via an applicator gas port on the tube proximal end, such as to allow withdrawing gas from the tube.

10. The system of claim 1, wherein the control infrastructure further comprises a gas supply fluidly coupled to the tube via the applicator gas port, such as to allow injecting gas into the tube.

11. The system of claim 1, further comprising processing and control circuitry, wherein the handle further comprises a user interface configured to allow a user to operate the discharge device, and wherein the processing and control circuitry is functionally associated with the waveform generator, the flyback amplifier, and the user interface, and is configured to coordinate operations thereof and to allow the user, via the user interface, to set and/or adjust electrical parameters characterizing the cold plasma discharge;
wherein the electrical parameters comprise one or more of an average power of the cold plasma discharge, an average electrical current amplitude, a frequency or frequencies of the pulses, a waveform or waveforms of the pulses, a duration or durations of the pulses, and a separation or separations between pairs of adjacent pulses.

12. The system of claim 1, wherein the handle further comprises a camera positioned to be at a line-of-sight from the target site when the handle is properly positioned with respect to the target site, such as to allow generating a cold plasma discharge directed at the target site, the camera being functionally associated with the processing and control circuitry.

13. A kit for treating skin tissue using cold plasma, the kit comprising the system of claim 3, with the applicator being detachably mounted on the handle, and a set of applicators, each of the applicators being configured to treat a respective group of skin or nail diseases and/or disorders having common dimensions, shape, and/or texture.

14. A method of treating skin and/or nail diseases and/or disorders in a target site on a subject, the method comprising stages of:
an initial stage comprising providing the system of claim 1;
a preparation stage comprising positioning the system such that the tube distal end of the applicator is at least in proximity to a target site on a subject; and
a treatment stage comprising closing an electrical circuit through the target site by generating a cold plasma discharge, wherein the cold plasma discharge has an average electrical current amplitude in the range of about 0.1 mA to about 10 mA and an average power in the range of about 0.1 µW to about 10 µW, so that the target site is not heated.

15. The method of claim 14, wherein the cold plasma discharge comprises a series of discharge pulses.

16. The method of claim 14, wherein the series of discharge pulses is induced by applying a voltage at the cap cathode of the applicator characterized by a series of pulses having a duty cycle in the range of 1% to 70%, wherein each pulse has a pulse width in the range of about 10 nsec to about 200 nsec, and wherein a frequency spectrum of the pulse includes one or more frequencies in the range of about 10 kHz to about 1 GHz.

17. The method of claim 14, wherein one or more of the pulses in the series of pulses are amplitude modulated, double-modulated, or harmonically modulated, and/or wherein one or more of the pulses in the series of pulses are amplitude modulated by a monotonically decreasing function.

18. The method of claim 14, further comprising a set up stage, performed prior to the preparation and treatment stage, wherein treatment parameters are determined, the treatment parameters at least comprising one or more parameters of the cold plasma discharge.

19. The method of claim 14, wherein the treatment stage further comprises a monitoring substage, wherein one or more plasma parameters are monitored, and a treatment adjustment substage, wherein one or more of the treatment parameters are adjusted contingent on at least one of the one or more monitored plasma parameters being outside a respective range.

* * * * *